United States Patent [19]

Devore et al.

[11] Patent Number: 5,470,993
[45] Date of Patent: Nov. 28, 1995

[54] TITANIUM(II) OR ZIRCONIUM(II) COMPLEXES AND ADDITION POLYMERIZATION CATALYSTS THEREFROM

[75] Inventors: David D. Devore; Francis J. Timmers; David R. Wilson, all of Midland, Mich.; Robert K. Rosen, Sugar Land, Tex.

[73] Assignee: The Dow Chemical Company, Midland, Mich.

[21] Appl. No.: 241,523

[22] Filed: May 12, 1994

Related U.S. Application Data

[63] Continuation-in-part of Ser. No. 230,051, Apr. 19, 1994, abandoned, which is a continuation-in-part of Ser. No. 82,197, Jun. 24, 1993, abandoned.

[51] Int. Cl.$^6$ .......................... C08F 4/642; C07F 17/00
[52] U.S. Cl. .......................... 556/11; 556/52; 556/7; 556/20; 556/28; 526/126; 526/127; 526/133; 526/134; 526/160; 526/170; 502/103; 502/117
[58] Field of Search .......................... 556/7, 11, 20, 556/28, 52; 526/126, 127, 133, 134, 160, 170; 502/103, 117

[56] References Cited

U.S. PATENT DOCUMENTS

| | | | |
|---|---|---|---|
| 5,198,401 | 3/1993 | Turner et al. | 502/155 |
| 5,321,106 | 6/1994 | La Pointe | 526/126 |
| 5,356,723 | 9/1994 | Neithamer et al. | 502/104 |
| 5,374,696 | 12/1994 | Rosen et al. | 526/126 |

FOREIGN PATENT DOCUMENTS

| | | |
|---|---|---|
| 416815 | 11/1991 | European Pat. Off. . |
| WO/9400500 | 1/1994 | WIPO . |
| WO/9407930 | 4/1994 | WIPO . |

OTHER PUBLICATIONS

Hawley's Condensed Chemical Dictionary, 11th Ed Van Nostrand Reinhold, New York, 1987, 385, 424, 854.
Yasuda, et al., *Organometallics*, 1, 388 (1982).
Yasuda et al., *Acc. Chem. Res.* 18, 120 (1985).
Erker, et al., *Adv. Organometl. Chem.*, 24, 1, (1985).
Blenkers, et al., *Organometallics*, 6, 459–469 (1987).

*Primary Examiner*—Mark Nagumo

[57] ABSTRACT

Novel titanium or zirconium complexes containing one and only one cyclic delocalized, anionic, π-bonded group wherein the metal is in the +2 formal oxidation state and having a bridged ligand structure, also referred to as constrained geometry complexes; catalytic derivatives of such complexes; methods of preparation; and the use thereof as catalysts for polymerizing olefins, diolefins and/or acetylenically unsaturated monomers.

14 Claims, 4 Drawing Sheets

TITANIUM(II) OR ZIRCONIUM(II) COMPLEXES AND ADDITION POLYMERIZATION CATALYSTS THEREFROM

CROSS-REFERENCE TO RELATED APPLICATION

This is a continuation-in-part of copending application Ser. No. 08/230,051, filed on Apr. 19, 1994, abandoned, which was a continuation-in-part of copending application Ser. No. 08/082,197, filed Jun. 24, 1993, abandoned. The teachings of the foregoing applications is hereby incorporated by reference.

BACKGROUND OF THE INVENTION

This invention relates to certain titanium and zirconium complexes comprising a single, cyclic, delocalized π-bonded ligand group wherein the metal of said complexes is in the +2 formal oxidation state. More particularly, this invention relates to such complexes wherein the metal is covalently bonded to the cyclic group via the delocalized π-system and also covalently bonded thereto via a divalent ligand group. Such complexes are referred to in the art as "constrained geometry" complexes. The invention further relates to techniques for preparing such complexes, to derivatives of such complexes that are catalysts useful for polymerizing olefins, diolefins and/or acetylenically unsaturated monomers, as well as such polymerization processes.

The preparation and characterization of certain biscyclopentadienyl zirconium and hafnium diene complexes are described in the following references: Yasuda, et al., *Organometallics*, 1, 388 (1982), (Yasuda I); Yasuda, et al. *Acc. Chem. Res.*, 18, 120 (1985), (Yasuda II); Erker, et al., *Adv. Organomet. Chem.*, 24, 1 (1985); and U.S. Pat. No. 5,198, 401. The latter reference describes the use of $Cp_2Zr$(diene) as an olefin polymerization catalyst in combination with ammonium borate cocatalysts.

The preparation of certain Ti, Zr, and Hf monocyclopentadienyl diene complexes lacking the present bridged ligand structure, was described in Yamamoto et al., *Organometallics*, 8, 105 (1989) (Yamamoto) and Blenkers, J, et al., *Organometallics*, 6, 459 (1987). Only the Hf complexes disclosed in the latter reference were described as having utility as catalyst components.

Constrained geometry metal complexes, including titanium complexes, and methods for their preparation are disclosed in U.S. application Ser. No. 545,403, filed Jul. 3, 1990, pending, (EP-A-416,815); U.S. application Ser. No. 547,718, filed Jul. 3, 1990, abandoned, (EP-A-468,651); U.S. application Ser. No. 702,475, filed May 20, 1991, abandoned, (EP-A-514,828); U.S. application Ser. No. 876, 268, filed May 1, 1992, pending, (EP-A-520,732) and U.S. application Ser. No. 8,003, filed Jan. 21, 1993, now U.S. Pat. No. 5,374,696 (WO93/19104), as well as U.S. Pat. No. 5,055,438, U.S. Pat. No. 5,057,475, U.S. Pat. No. 5,096,867, U.S. Pat. No. 5,064,802 and U.S. Pat. No. 5,132,380. The teachings of all the foregoing patents, publications and patent applications is hereby incorporated by reference.

Despite the advance in the art brought about by the foregoing constrained geometry complexes, the adaption of such technology to Group 4 metals in the +2 formal oxidation state has previously been unknown.

SUMMARY OF THE INVENTION

According to the present invention there are provided metal complexes containing one and only one cyclic, delocalized, anionic, π-bonded group, said complexes corresponding to the formula:

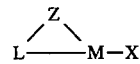

wherein:

M is titanium or zirconium in the +2 formal oxidation state;

L is a group containing a cyclic, delocalized, anionic, π-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 nonhydrogen atoms; and X is a neutral, conjugated or nonconjugated diene, optionally substituted with one or more hydrocarbyl groups, said X having up to 40 carbon atoms and forming a π-complex with M.

Additionally according to the present invention there is provided a process for preparing a metal complex containing one and only one cyclic, delocalized π-bonded group, said complex corresponding to the formula:

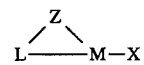

wherein M, L, Z and X are as previously defined, comprising:

contacting a compound according to the formula $M(X^*)_2$ or a solvated adduct thereof wherein $X^*$ is halo and M is as previously defined, with a conjugated or nonconjugated $C_{4-40}$ diene compound corresponding to X and a source of a dianion ligand, $(Z—L)^{-2}$.

In a preferred embodiment the compound according to the formula $M(X^*)_2$ is prepared by contacting a compound according to the formula $M^*(X^*)_3$ or $M^{**}(X^*)_4$, or a solvated adduct thereof, in a solvent, with a reducing agent under reducing conditions wherein, $M^*$ is titanium or zirconium in the +3 formal oxidation state;

$M^{**}$ is titanium or zirconium in the +4 formal oxidation state; and $X^*$ is as previously defined.

In another embodiment of the present invention there is provided a process for preparing a metal complex containing one and only one cyclic, delocalized π-bonded group, said complex corresponding to the formula:

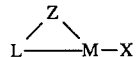

wherein M, L, Z and X are as previously defined, the steps of the process comprising:

1) a) contacting a conjugated or nonconjugated $C_{4-40}$ diene compound with a metal complex corresponding to the formula:

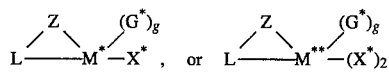

wherein,
M* is titanium or zirconium in the +formal oxidation state,
M** is titanium or zirconium in the +4 formal oxidation state, and
X* is halo;
G* is a neutral Lewis base selected from amines, phosphines and ethers said G having from 3 to 20 non-hydrogen atoms;
L and Z are as previously defined; and
g is a number from 0 to 3, in an inert solvent, and
b) contacting the resulting mixture with a reducing agent, or 2) a) contacting a conjugated or nonconjugated $C_{4-40}$ diene compound with a reducing agent in a suitable noninterfering solvent, and
b) contacting the resulting mixture with a metal complex corresponding to the formula:

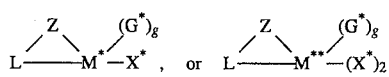

wherein
M* is titanium or zirconium in the +formal oxidation state;
M** is titanium or zirconium in the +4 formal oxidation state; and
X* is halo;
G* is a neutral Lewis base selected from amines, phosphines and ethers, said G having from 3 to 20 non-hydrogen atoms;
L and Z are as previously defined; and
g is a number from 0 to 3.

Further according to the present invention there are provided catalysts for polymerization of addition polymerizable monomers comprising a combination of one or more of the above metal complexes and one or more activating cocatalysts or activating techniques.

The present invention also provides a polymerization process comprising contacting one or more addition polymerizable monomers with a catalyst comprising one or more of the above metal complexes and one or more activating cocatalysts or activating techniques. The polymerization may be performed under solution, suspension, slurry, or gas phase process conditions, and the catalyst or individual components thereof may be used in a heterogeneous, i.e. a supported state, or in a homogeneous state as dictated by process conditions. The catalyst can be used in combination with one or more additional catalysts of the same or different nature either simultaneously in the same reactor or sequentially in separate reactors.

Catalysts prepared from the complexes of the present invention possess improved catalytic properties compared to corresponding complexes wherein the metal is in the +4 formal oxidation state. Surprisingly, the present complexes retain high catalytic efficiency at elevated temperatures compared to similar catalysts wherein the metal is in the +4 formal oxidation state. Also, the present complexes under similar processing conditions give higher molecular weight polymers than are produced using catalysts wherein the metal is in the +4 formal oxidation state. In addition, the complexes are compatible with and may be used in combination with alkylaluminum compounds which may be employed to scavenge monomer impurities without detrimental effect to their catalytic properties. Finally, the present complexes are more readily, and thus more efficiently, activated by common activating cocatalysts, such as strong Lewis acids, than are corresponding complexes wherein the metal is in the +4 formal oxidation state.

DETAILED DESCRIPTION

Figure 1:
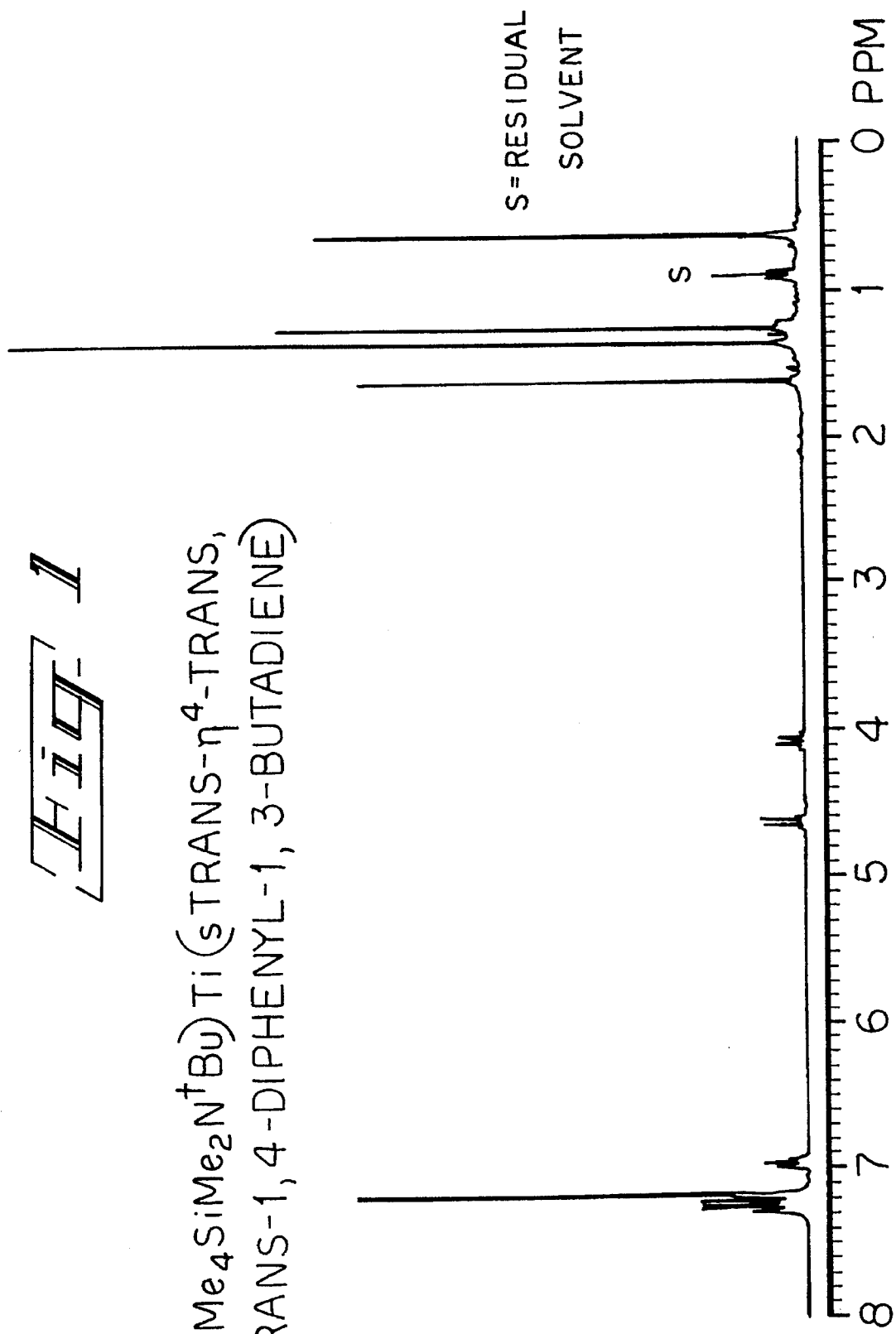
FIGS. 1–3 show $^1$H NMR spectra of the metal complexes of Examples A1, 17 and 18 respectively.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The diene group, X, does not decompose under reaction conditions used to prepare the complexes of the invention. Under subsequent polymerization conditions, or in the formation of catalytic derivatives of the present complexes, the diene group, X, may undergo chemical reactions or be replaced by another ligand.

The present titanium and zirconium complexes contain a neutral diene ligand which is coordinated via π-complexation through the diene double bonds, and not through a metallacycle containing σ-bonds (σ-bound diene) where the metal is in the +4 formal oxidation state. Such a distinction is readily determined by X-ray crystallography or by NMR spectral characterization according to the techniques of Yasuda I, Yasuda II, and Erker, et al., Supra, as well as the references cited therein. By the term "π-complex" is meant both the donation and back acceptance of electron density by the ligand are accomplished using ligand π-orbitals, i.e., the diene is π-bound (π-bound diene).

A suitable method of determining the existence of a π-complex in conjugated diene containing metal complexes is the measurement of metal-carbon atomic spacings for the two terminal carbons of the conjugated diene using common X-ray crystal analysis techniques. For titanium containing complexes, atomic spacings for the two terminal carbons from the metal atom greater than 2.205 Å indicate that a π-complex exists. For zirconium complexes, atomic spacings greater than 2.350 Å indicate that a π-complex exists. Alternatively, measurements of atomic spacings between the metal and C1, C2, C3, C4 (M–C1, M–C2, M–C3, M–C4, respectively) (where C1 and C4 are the terminal carbons of the 4 carbon conjugated diene group and C2 and C3 are the internal carbons of the of the 4 carbon conjugated diene group) may be made. If the difference between these bond distances, Δd, using the following formula:

$$\Delta d = \left[ \left\{ \frac{(M-C1)+(M-C4)}{2} \right\} - \right.$$

$$\left\{ \frac{(M-C2)+(M-C3)}{2} \right\} \Bigg]$$

is greater than −0.15 Å, the diene is considered to form a π-complex with M. The existence of either property is determinative of the existence of a π-complex.

Examples wherein the above method for determination of π-complexes has been applied to prior art compounds are found in Eker, et al., *Angew. Chem, Int. Ed. Encl.*, 23,455–456 (1984) (Erker et al.) and Yamamoto, Supra. In the former reference ($\eta^3$-allyl)($\eta^4$-butadiene)($\eta^5$-cyclopentadienyl)zirconium was crystallographically characterized. The M–C1 and M–C4 distances were both 2.360 (±0.005) Å. The M–C2 and M–C3 distances were both 2.463 (±0.005) Å, giving a Δd of −0.103 Å. In the latter reference ($\eta^5$-pentamethylcyclopentadienyl)($\eta^4$-1,4-diphenyl-1,3-butadiene)titanium chloride was shown to have M–C1 and M–C4 distances of 2.233 (±0.006) Å. The M–C2 and M–C3 distances were both 2.293 (±0.005) Å, giving a Δd of −0.060 Å. Erker et al. also disclosed bis(cyclopentadienyl)zirconium (2,3-dimethyl-1,3-butadiene). In this complex the M–C1 and M–C4 distances were 2.300 Å. The M–C2 and M–C3 distances were both 2.597 Å, giving a Δd of −0.297 Å. Accordingly, this complex contains a σ-bound diene and the zirconium is in the +4 formal oxidation state. In the use of such X-ray crystal analysis techniques at least "good" and preferably "excellent" determination quality as defined by G. Stout et al., *X-ray Structure Determination, A Practical Guide*, Macmillan Co., pg 430–431, (1968) is used.

Alternatively, complexes of the present invention wherein X is a conjugated diene in the form of a π-complex and M is in the +2 formal oxidation state are identified using nuclear magnetic resonance spectroscopy techniques. The teachings of Erker, et al., supra, C. Krüger, et al. *Organometallics*, 4, 215–223, (1985), and Yasuda I, supra, disclose these well known techniques for distinguishing between π-bound complexes and metallocyclic coordination or σ-bound diene complexes. The teachings of the foregoing references related to π-bound complexes is hereby incorporated by reference.

When the foregoing techniques are indeterminate of the existence of π-complexes, the relevant atomic spacings may be determinable by a restricted Hartree-Fock method, which is a standard method of molecular orbital (MO) theory, as explained hereinafter.

Not withstanding the foregoing statement, it is to be understood that when X is a conjugated diene, the present complexes may be formed and utilized as a mixture of π-bound diene complexes and σ-bound diene complexes. Preferably the complexes of the present invention are present in a molar amount from greater than 10 to 100 percent, more preferably in a molar amount from 50 to 100 percent, most preferably in a molar amount from 60 to 100 percent, based on the total amount of complexes present. Techniques for separation and purification of π-bound diene complexes complex from mixtures of π-bound diene complexes and σ-bound diene complexes are known in the art and disclosed for example in the previously mentioned Yasuda I, Yasuda II, and Erker, et al. references and may be employed if desired to prepare and isolate the complexes in greater purity.

Inasmuch as the complexes can contain only one cyclic delocalized, anionic, π-bonded group, it follows that Z or X, singly or in combination, cannot comprise a cyclopentadienyl group or other cyclic delocalized π-bonded group.

Preferred metal coordination complexes according to the present invention correspond to the formula:

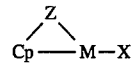

wherein Z, M and X are as previously defined; and

Cp is a $C_5H_4$ group bound to Z and bound in an $\eta^5$ bonding mode to M or is such an $\eta^5$ bound group substituted with from one to four substituents independently selected from hydrocarbyl, silyl, germyl, halo, cyano, and combinations thereof, said substituent having up to 20 nonhydrogen atoms, and optionally, two such substituents (except cyano or halo) together cause Cp to have a fused ring structure.

More preferred metal coordination complexes according to the present invention correspond to the formula:

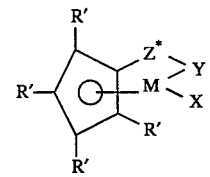

wherein:

R' each occurrence is independently selected from hydrogen, hydrocarbyl, silyl, germyl, halo, cyano, and combinations thereof, said R' having up to 20 nonhydrogen atoms, and optionally, two R' groups (where R' is not hydrogen, halo or cyano) together form a divalent derivative thereof connected to adjacent positions of the cyclopentadienyl ring to form a fused ring structure;

X is a neutral $\eta^4$-bonded diene group having up to 30 non-hydrogen atoms, which forms a π-complex with M;

Y is —O—, —S—, —NR*—, —PR*—;

M is titanium or zirconium in the +2 formal oxidation state;

Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$; wherein:

R* each occurrence is independently hydrogen, or a member selected from hydrocarbyl, silyl, halogenated alkyl, halogenated aryl, and is combinations thereof, said R* having up to 10 non-hydrogen atoms, and optionally, two R* groups from Z* (when R* is not hydrogen), or an R* group from Z* and an R* group from Y form a ring system.

Preferably, R' independently each occurrence is hydrogen, hydrocarbyl, silyl, halo and combinations thereof said R' having up to 10 non-hydrogen atoms, or two R' groups (when R' is not hydrogen or halo) together form a divalent derivative thereof; most preferably, R' is hydrogen, methyl, ethyl, propyl, butyl, pentyl, hexyl, (including where appropriate all isomers), cyclopentyl, cyclohexyl, norbornyl, benzyl, or phenyl or two R' groups (except hydrogen) are linked together, the entire $C_5R'_4$ group thereby being, for example, an indenyl, tetrahydroindenyl, fluorenyl, tetrahydrofluorenyl, or octahydrofluorenyl group.

Further preferably, at least one of R' or R* is an electron donating moiety. By the term "electron donating" is meant that the moiety is more electron donating than hydrogen. Thus, highly preferably Y is a nitrogen or phosphorus containing group corresponding to the formula —N(R")— or —P(R")—, wherein R" is $C_{1-10}$ hydrocarbyl.

Examples of suitable X groups include: s-trans-η⁴-1,4-diphenyl-1,3-butadiene; s-trans-η⁴-3-methyl-1,3-pentadiene; s-trans-η⁴-1,4-dibenzyl-1,3-butadiene; s-trans-η⁴-2,4-hexadiene; s-trans-η⁴-1,3-pentadiene; s-trans-η⁴-1,4-ditolyl- 1,3-butadiene; s-trans-η⁴-1,4-bis(trimethylsilyl)-1,3-butadiene; s-cis-η⁴- 1,4-diphenyl-1,3-butadiene; s-cis-η⁴-3-methyl-1,3-pentadiene; s-cis-η⁴-1,4-dibenzyl- 1,3-butadiene; s-cis-η⁴-2,4-hexadiene; s-cis-η⁴-1,3-pentadiene; s-cis-η⁴- 1,4-ditolyl-1,3-butadiene; and s-cis-η⁴-1,4-bis(trimethylsilyl)-1,3-butadiene, said s-cis diene group forming a π-complex as defined herein with the metal.

Most highly preferred metal coordination complexes are amidosilane- or amidoalkanediyl- compounds corresponding to the formula:

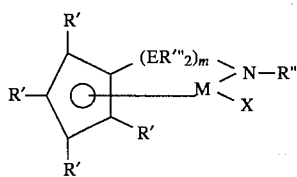

wherein:

M is titanium;

X is s-trans-η⁴-1,4-diphenyl-1,3-butadiene; s-trans-η⁴-3-methyl-1,3-pentadiene; s-trans-η⁴-1,4-dibenzyl-1,3-butadiene; s-trans-η⁴-1,3-pentadiene; s-trans-η⁴-2,4-hexadiene; s-trans-η⁴-1,4-ditolyl-1,3-butadiene; s-trans-η⁴- 1,4-bis(trimethylsilyl)-1,3-butadiene; s-cis-η⁴-1,4-diphenyl-1,3-butadiene; s-cis-η⁴- 3-methyl-1,3-pentadiene; s-cis-η⁴-1,4-dibenzyl-1,3-butadiene; s-cis-η⁴-1,3-pentadiene; s-cis-η⁴-2,4-hexadiene; s-cis-η⁴-1,4-ditolyl-1,3-butadiene; or s-cis-η⁴- 1,4-bis(trimethylsilyl)-1,3-butadiene, said s-cis diene group forming a π-complex as defined herein with the metal;

R' each occurrence is independently selected from hydrogen, silyl, hydrocarbyl and combinations thereof, said R' having up to 10 carbon or silicon atoms, or two such R' groups on the substituted cyclopentadienyl group (when R' is not hydrogen) together form a divalent derivative thereof connected to adjacent positions of the cyclopentadienyl ring;

R" is C₁₋₁₀ hydrocarbyl;

R'" is independently each occurrence hydrogen or C₁₋₁₀ hydrocarbyl;

E is independently each occurrence silicon or carbon; and m is 1 or 2.

Examples of the metal complexes according to the present invention include compounds wherein R" is methyl, ethyl, propyl, butyl, pentyl, hexyl, (including all isomers of the foregoing where applicable), cyclododecyl, norbornyl, benzyl, or phenyl; (ER'"₂)ₘ is dimethylsilane, or ethanediyl; and the cyclic delocalized π-bonded group is cyclopentadienyl, tetramethylcyclopentadienyl, indenyl, tetrahydroindenyl, fluorenyl, tetrahydrofluorenyl or octahydrofluorenyl.

If the aforementioned empirical techniques for measuring whether a complex possesses the requisite diene π-complex configuration are indeterminate, a restricted Hartree-Fock method may be utilized to determine molecular spacings. Such Hartree-Fock methods are well known having been disclosed by: W. J. Hehre, L. Radom, P. R. Schleyer, and J. A. Pople, *Ab Initio Molecular Orbital Theory* (Wiley, New York, 1986); K. D. Dobbs and W. J. Hehre, "Molecular Orbital Theory of the Properties of Inorganic and Organo- metallic Compounds, 5, Extended Basis Sets For First-row Transition Metals" [3-21G, 3- 21G*, Sc-Zn], *J. Comput. Chem.* 8, 861 (1987); K. D. Dobbs and W. J. Hehre, Molecular Orbital Theory of the Properties of Inorganic and Organometallic Compounds, 5, Extended Basis Sets For First-row Transition Metals. [3-21G, 3- 21G*,Sc-Zn], *J. Comput. Chem.* 9, 801 (1988) (Erratum to above); and K. D. Dobbs and W. J. Hehre, Molecular Orbital Theory of the Properties of Inorganic and Organometallic Compounds, 6, Extended Basis Sets for Second-row Transition Metals [3-21G, 3-21G*, Y-Cd], *J. Comput. Chem.* 8, 880–93 (1987).

According to the technique as utilized herein, solutions to the quantum mechanical equations for the electronic structures of isolated molecules in the gas phase are solved according to the well known, rigorous, ab initio method, using a 3-21ddG basis set. The 3-21ddG basis set uses all of the functions from 3-21 G, and adds a diffuse d function to each transition metal atom, as disclosed by: P. J. Hay, Gaussian Basis Sets for Molecular Calculations, the Representation of 3d Orbitals in Transition-metal Atoms, [3-21ddG], *J. Chem. Phys.* 66, 4377–84 (1977); A. K. Rappe, T. A. Smedley, and W. A. Goddard, III, Flexible d Basis Sets for Scandium Through Copper [3-21ddG], *J. Phys. Chem.* 85, 2607–11 (1981); and P. J. Hay and W. R. Wadt, Ab Initio Effective Core Potentials for Molecular Calculations, Potentials for the Transition Metal Atoms Scandium to Mercury, [3-21ddG], *J. Chem. Phys.* 82, 270–83 (1985). For transition metals, it is well known that the diffuse d function improves the treatment of the various possible electronic configurations. The exponent of the added function is determined from the ratios of values for the other exponents. The diffuse d exponents added are: Ti, 0.101; Zr, 0.055.

The HF/3-21ddG calculations are carried out using GAUSSIAN 92™, Revision D.2, available from Gaussian, Inc., Carnegie Office Park, Building 6, Pittsburgh, Pa. 15106, or equivalent program. The technique is further disclosed in J. B. Foresman and A. Frisch, *Exploring Chemistry with Electronic Structure Methods: A Guide to Using Gaussian,* Gaussian, Inc., Pittsburgh, Pa., 1993. The teachings of all of the foregoing references related to molecular calculations is hereby incorporated by reference.

More particularly, the structure of a complex is calculated as follows:

1. An initial structure is constructed using a molecular modeling program such as POLYGRAF™ Molecular Design and Analysis Program, version 3.21 (06/01/93), available from Molecular Simulations, Inc., 16 New England Executive Park, Burlington, Mass. 01803-5297, or equivalent program.

2. Optimized structures are obtained by an iterative method using the GAUSSIAN™ 92 program, or subsequent versions thereof. In each optimization cycle, the energy and atomic forces (energy gradients) are used to generate a new, refined structure or atomic positions. The final optimized structure is obtained when the displacements and forces of all atoms meet convergence thresh holds of 0.00180 atomic units and 0.00045 atomic units, respectively. At this point, the total energy is minimized with respect to all degrees of freedom (molecular structure variables). For nonlinear is molecules, there are 3n–6 degrees of freedom, where n is the number of atoms. These 3n–6 degrees of freedom are expressed as a combination of atomic coordinates (x, y, z) and internal coordinates (bond lengths, bond angles, and torsion angles).

3. The total energies for various isomers calculated by HF/3-21ddG are then compared to determine the lowest energy isomer and the atomic coordinates for that isomer are selected for determination of atomic spacings, Δd, according to the previously disclosed formula.

For organotitanium or organozirconium compounds such as the present, the HF/3-21ddG structures have been found to be accurate to better than 0.2 Å, 0.06 Å, 3°, and 5°, for the atomic positions, bond lengths, bond angles, and torsion angles, respectively, as compared to structures obtained by x-ray diffraction.

Specific metal complexes included within the present invention are:

(tert-butylamido)(tetramethyl-$\eta^5$-cyclopentadienyl)-1,2-ethanediyltitanium s-trans-$\eta^4$-1,4-diphenyl-1,3-butadiene; (tert-butylamido)(tetramethyl-$\eta^5$-cyclopentadienyl)-1,2-ethanediyltitanium s-trans-$\eta^4$-1,4-dibenzyl-1,3-butadiene; (tert-butylamido)(tetramethyl-$\eta^5$-cyclopentadienyl)-1,2-ethanediyltitanium s-trans-$\eta^4$-2,4-hexadiene; (tert-butylamido)(tetramethyl-$\eta^5$-cyclopentadienyl)- 1,2-ethanediyltitanium s-trans-$\eta^4$-3-methyl-1,3-pentadiene; (tert-butylamido)(tetramethyl-$\eta^5$-cyclopentadienyl)-1,2-ethanediyltitanium s-trans-$\eta^4$-1,3-pentadiene; (tert-butylamido)(tetramethyl-$\eta^5$-cyclopentadienyl)-1,2-ethanediyltitanium s-trans-$\eta^4$-1,4-bis(trimethylsilyl)- 1,3-butadiene;

(methylamido)(tetramethyl-$\eta^5$-cyclopentadienyl)-1,2-ethanediyltitanium s-trans-$\eta^4$-1,4-diphenyl-1,3-butadiene; (methylamido)(tetramethyl-$\eta^5$-cyclopentadienyl)-1,2-ethanediyltitanium s-trans-$\eta^4$-1,4-dibenzyl-1,3-butadiene; (methylamido)(tetramethyl-$\eta^5$-cyclopentadienyl)-1,2-ethanediyltitanium s-trans-$\eta^4$-2,4-hexadiene; (methylamido)(tetramethyl-$\eta^5$-cyclopentadienyl)-1,2-ethanediyltitanium s-trans-$\eta^4$-3-methyl-1,3-pentadiene; (methylamido)(tetramethyl-$\eta^5$-cyclopentadienyl)- 1,2-ethanediyltitanium s-trans-$\eta^4$-1,3-pentadiene; (methylamido)(tetramethyl-$\eta^5$-cyclopentadienyl)-1,2-ethanediyltitanium s-trans-$\eta^4$-1,4-bis(trimethylsilyl)-1,3-butadiene;

(phenylamido)(tetramethyl-$\eta^5$-cyclopentadienyl)-1,2-ethanediyltitanium s-trans-$\eta^4$-1,4-diphenyl-1,3-butadiene; (phenylamido)(tetramethyl-$\eta^5$-cyclopentadienyl)-1,2-ethanediyltitanium s-trans-$\eta^4$-1,4-dibenzyl-1,3-butadiene; (phenylamido)(tetramethyl-$\eta^5$-cyclopentadienyl)-1,2-ethanediyltitanium s-trans-$\eta^4$-2,4-hexadiene; (phenylamido)(tetramethyl-$\eta^5$-cyclopentadienyl)- 1,2-ethanediyltitanium s-trans-$\eta^4$-3-methyl-1,3-pentadiene; (phenylamido)(tetramethyl-$\eta^5$-cyclopentadienyl)-1,2-ethanediyltitanium s-trans-$\eta^4$-1,3-pentadiene; (phenylamido)($\eta^5$-cyclopentadienyl)-1,2-ethanediyltitanium s-trans-$\eta^4$-1,4-bis(trimethylsilyl)-1,3-butadiene;

(t-butylamido)($\eta^5$-cyclopentadienyl)-1,2-ethanediyltitanium s-trans-$\eta^4$-1,4-dibenzyl-1,3-butadiene; (t-butylamido)($\eta^5$-cyclopentadienyl)-1,2-ethanediyltitanium s-trans-$\eta^4$-2,4-hexadiene; (benzylamido)(tetramethyl-$\eta^5$-cyclopentadienyl)- 1,2-ethanediyltitanium s-trans-$\eta^4$-1,4-diphenyl-1,3-butadiene; (benzylamido)(tetramethyl-$\eta^5$-cyclopentadienyl)-1,2-ethanediyltitanium s-trans-$\eta^4$-1,4-dibenzyl-1,3-butadiene; (benzylamido)(tetramethyl-$\eta^5$-cyclopentadienyl)-1,2-ethanediyltitanium s-trans-$\eta^4$-2,4-hexadiene; (benzylamido)(tetramethyl-$\eta^5$-cyclopentadienyl)-1,2-ethanediyltitanium s-trans-$\eta^4$-3-methyl-1,3-pentadiene; (benzylamido)(tetramethyl-$\eta^5$-cyclopentadienyl)-1,2-ethanediyltitanium s-trans-$\eta^4$-1,3-pentadiene; (t-butylamido)($\eta^5$-cyclopentadienyl)-1,2-ethanediyltitanium s-trans-$\eta^4$- 1,4-bis(trimethylsilyl)-1,3-butadiene;

(cyclododecylamido)(tetramethyl-$\eta^5$-cyclopentadienyl)-1,2-ethanediyltitanium s-trans-$\eta^4$-1,4-diphenyl-1,3-butadiene; (cyclododecylamido)(tetramethyl-$\eta^5$-cyclopentadienyl)-1,2-ethanediyltitanium s-trans-$\eta^4$-1,4-dibenzyl-1,3-butadiene; (cyclododecylamido)(tetramethyl-$\eta^5$-cyclopentadienyl)- 1,2-ethanediyltitanium s-trans-$\eta^4$-2,4-hexadiene; (cyclododecylamido)(tetramethyl-$\eta^5$-cyclopentadienyl)-1,2-ethanediyltitanium s-trans-$\eta^4$-3-methyl-1,3-pentadiene; (cyclododecyl)(tetramethyl-$\eta^5$-cyclopentadienyl)- 1,2-ethanediyltitanium s-trans-$\eta^4$-1,3-pentadiene; (cyclododecylamido)(tetramethyl-$\eta^5$-cyclopentadienyl)-1,2-ethanediyltitanium s-trans-$\eta^4$-1,4-bis(trimethylsilyl)-1,3-butadiene;

(phenylphosphido)(tetramethyl-$\eta^5$-cyclopentadienyl)-1,2-ethanediyltitanium s-trans-$\eta^4$-1,4-diphenyl-1,3-butadiene; (phenylphosphido)(tetramethyl-$\eta^5$-cyclopentadienyl)-1,2-ethanediyltitanium s-trans-$\eta^4$-3-methyl-1,3-pentadiene; (phenylphosphido)(tetramethyl-$\eta^5$-cyclopentadienyl)-1,2-ethanediyltitanium s-trans-$\eta^4$-1,3-pentadiene; (phenylamido)(tetramethyl-$\eta^5$-cyclopentadienyl)- 1,2-ethanediyltitanium s-trans-$\eta^4$-1,4-bis(trimethylsilyl)-1,3-butadiene;

(tert-butylamido)(tetramethyl-$\eta^5$-cyclopentadienyl)dimethylsilanetitanium s-trans-$\eta^4$-1,4-diphenyl-1,3-butadiene; (tert-butylamido)(tetramethyl-$\eta^5$-cyclopentadienyl)dimethylsilanetitanium s-trans-$\eta^4$-1,4-dibenzyl-1,3-butadiene; (tert-butylamido)(tetramethyl-$\eta^5$-cyclopentadienyl)dimethylsilanetitanium s-trans-$\eta^4$-2,4-hexadiene; (tert-butylamido)(tetramethyl-$\eta^5$-cyclopentadienyl)dimethylsilanetitanium s-trans-$\eta^4$-3-methyl-1,3-pentadiene; (tert-butylamido)(tetramethyl-$\eta^5$-cyclopentadienyl)dimethylsilanetitanium s-trans-$\eta^4$-1,3-pentadiene; (t-butylamido)(tetramethyl-$\eta^5$-cyclopentadienyl)dimethylsilanetitanium s-trans-$\eta^4$-1,4-bis(trimethylsilyl)-1,3-butadiene;

(methylamido)(tetramethyl-$\eta^5$-cyclopentadienyl)dimethylsilanetitanium s-trans-$\eta^4$-1,4-diphenyl-1,3-butadiene; (methylamido)(tetramethyl-$\eta^5$-cyclopentadienyl)dimethylsilanetitanium s-trans-$\eta^4$-1,4-dibenzyl- 1,3-butadiene; (methylamido)(tetramethyl-$\eta^5$-cyclopentadienyl)dimethylsilanetitanium s-trans-$\eta^4$-2,4-hexadiene; (methylamido)(tetramethyl-$\eta^5$-cyclopentadienyl)dimethylsilanetitanium s-trans-$\eta^4$-3-methyl-1,3-pentadiene; (methylamido)(tetramethyl-$\eta^5$-cyclopentadienyl)dimethylsilanetitanium s-trans-$\eta^4$-1,3-pentadiene; (methylamido)(tetramethyl-$\eta^5$-cyclopentadienyl)-dimethylsilanetitanium s-trans-$\eta^4$-1,4-bis(trimethylsilyl)-1,3-butadiene;

(phenylamido)(tetramethyl-$\eta^5$-cyclopentadienyl)dimethylsilanetitanium s-trans-$\eta^4$-1,4-diphenyl-1,3-butadiene; (phenylamido)(tetramethyl-$\eta^5$-cyclopentadienyl)dimethylsilanetitanium s-trans-$\eta^4$-1,4-dibenzyl-1,3-butadiene; (phenylamido)(tetramethyl-$\eta^5$-cyclopentadienyl)dimethylsilanetitanium s-trans-$\eta^4$-2,4-hexadiene; (phenylamido)(tetramethyl-$\eta^5$-cyclopentadienyl)dimethylsilanetitanium s-trans-$\eta^4$-3-methyl-1,3-pentadiene; (phenylamido)(tetramethyl-$\eta^5$-cyclopentadienyl)dimethylsilanetitanium s-trans-$\eta^4$-1,3-pentadiene; (phenylamido)(tetramethyl-$\eta^5$-cyclopentadienyl)dimethylsilanetitanium s-trans-$\eta^4$-1,4-bis(trimethylsilyl)-1,3-butadiene;

(cyclododecylamido)(tetramethyl-$\eta^5$-cyclopentadienyl)dimethylsilanetitanium s-trans-$\eta^4$-1,4-diphenyl-1,3-butadiene; (cyclodecylamido)(tetramethyl-$\eta^5$-cyclopentadienyl)dimethylsilanetitanium s-trans-$\eta^4$-1,4-dibenzyl-1,3-butadiene; (cyclododecylamido)(tetramethyl-$\eta^5$scyclopentadienyl)dimethylsilanetitanium s-trans-$\eta^4$-2,4-hexadiene; (cyclododecylamido)(tetramethyl-$\eta^5$-cyclopentadienyl)dimethylsilanetitanium s-trans-$\eta^4$-3-methyl-1,3-pentadiene; (cyclododecylamido)(tetramethyl-$\eta^5$-cyclopentadienyl)dimethylsilanetitanium s-trans-$\eta^4$-1,3-pentadiene; (cyclododecylamido)(tetramethyl-$\eta_5$-cyclopentadienyl)-dimethylsilanetitanium s-trans-$\eta^4$-1,4-bis(trimethylsilyl)-1,3-butadiene;

(t-butylamido)($\eta^5$-cyclopentadienyl)dimethylsilanetitanium s-trans-$\eta$-1,4-diphenyl-1,3-butadiene; (tert-butylamido)($\eta^5$-cyclopentadienyl)dimethylsilanetitanium s-trans-$\eta^4$-1,4-dibenzyl-1,3-butadiene; (tert-butylamido)($\eta^5$-cyclopentadienyl)dimethylsilanetitanium s-trans-$\eta^4$-2,4-hexadiene; (t-butylamido)($\eta^5$-cyclopentadienyl)dimethylsilanetitanium s-trans-$\eta^4$-3-methyl-1,3-pentadiene; (t-butylamido)($\eta^5$-cyclopentadienyl)dimethylsilanetitanium s-trans-$\eta^4$-1,3-pentadiene; (t-butylamido)($\eta^5$-cyclopentadienyl)dimethylsilanetitanium s-trans-$\eta^4$-1,4-bis(trimethylsilyl)-1,3-butadiene;

(benzylamido)(tetramethyl-$\eta^5$-cyclopentadienyl)dimethylsilanetitanium s-trans-$\eta^4$-1,4-diphenyl-1,3-butadiene; (benzylamido)(tetramethyl-$\eta^5$-cyclopentadienyl)dimethylsilanetitanium s-trans-$\eta^4$-1,4-dibenzyl-1,3-butadiene; (benzylamido)(tetramethyl-$\eta^5$-cyclopentadienyl)dimethylsilanetitanium s-trans-$\eta^4$-2,4-hexadiene; (benzylamido)(tetramethyl-$\eta^5$-cyclopentadienyl)dimethylsilanetitanium s-trans-$\eta^4$-3-methyl-1,3-pentadiene; (benzylamido)(tetramethyl-$\eta^5$-cyclopentadienyl)dimethylsilanetitanium s-trans-$\eta^4$-1,3-pentadiene; (benzylamido)(tetramethyl-$\eta^5$-cyclopentadienyl)dimethylsilanetitanium s-trans-$\eta^4$-1,4-bis(trimethylsilyl)-1,3-butadiene;

(phenylphosphido)(tetramethyl-$\eta^5$-cyclopentadienyl)dimethylsilanetitanium s-trans-$\eta^4$-1,4-diphenyl-1,3-butadiene; (phenylphosphido)(tetramethyl-$\eta^5$-cyclopentadienyl)dimethylsilanetitanium s-trans-$\eta^4$-1,4-dibenzyl-1,3-butadiene; (phenylphosphido)(tetramethyl-$\eta^5$-cyclopentadienyl)dimethylsilanetitanium s-trans-$\eta^4$-2,4-hexadiene; (phenylphosphido)(tetramethyl-$\eta^5$-cyclopentadienyl)dimethylsilanetitanium s-trans-$\eta^4$-3-methyl-1,3-pentadiene, (phenylphosphido)(tetramethyl-$\eta^5$-cyclopentadienyl)dimethylsilanetitanium s-trans-$\eta^4$-1,3-pentadiene; (phenylphosphido)(tetramethyl-$\eta^5$-cyclopentadienyl)dimethylsilanetitanium s-trans-$\eta^4$-1,4-bis(trimethylsilyl)-1,3-butadiene;

(tert-butylamido)($\eta^5$-indenyl)-1,2-ethanediyltitanium s-trans-$\eta^4$-1,4-diphenyl-1,3-butadiene; (tert-butylamido)(tetrahydroindenyl)-1,2-ethanediyltitanium s-trans-$\eta^4$-1,4-dibenzyl-1,3-butadiene; (tert-butylamido)($\eta^5$-fluorenyl)-1,2-ethanediyltitanium s-trans-$\eta^4$-2,4-hexadiene; (tert-butylamido)($\eta^5$-indenyl)-1,2-ethanediyltitanium s-trans-$\eta^4$-3-methyl-1,3-pentadiene; (tert-butylamido)($\eta^5$-indenyl)-1,2-ethanediyltitanium s-trans-$\eta^4$-1,3-pentadiene; (t-butylamido)(tetramethyl-$\eta^5$-cyclopentadienyl)dimethylsilanetitanium s-trans-$\eta^4$-1,4-bis(trimethylsilyl)-1,3-butadiene;

(methylamido)($\eta^5$-tetrahydroindenyl)-1,2-ethanediyltitanium s-trans-$\eta^4$-1,4-diphenyl-1,3-butadiene; (methylamido)($\eta^5$-indenyl)-1,2-ethanediyltitanium s-trans-$\eta^4$-1,4-dibenzyl-1,3-butadiene; (methylamido)($\eta^5$-indenyl)-1,2-ethanediyltitanium s-trans-$\eta^4$-2,4-hexadiene; (methylamido)($\eta^5$-fluorenyl)-1,2-ethanediyltitanium s-trans-$\eta^4$-3-methyl-1,3-pentadiene; (methylamido)($\eta^5$-fluorenyl)-1,2-ethanediyltitanium s-trans-$\eta^4$-1,3-pentadiene; (methylamido)($\eta^5$-tetrahydroindenyl)-1,2-ethanediyltitanium s-trans-$\eta^4$-1,4-bis(trimethylsilyl)-1,3-butadiene;

(phenylamido)($\eta^5$-octahydrofluorenyl)-1,2-ethanediyltitanium s-trans-$\eta^4$-1,4-diphenyl-1,3-butadiene; (phenylamido)($\eta^5$-indenyl)-1,2-ethanediyltitanium s-trans-$\eta^4$-1,4-dibenzyl-1,3-butadiene; (phenylamido)($\eta^5$-fluorenyl)-1,2-ethanediyltitanium s-trans-$\eta^4$-2,4-hexadiene; (phenylamido)($\eta^5$-tetrahydroindenyl)-1,2-ethanediyltitanium s-trans-$\eta^4$-3-methyl-1,3-pentadiene; (phenylamido)($\eta^5$-tetrahydroindenyl)-1,2-ethanediyltitanium s-trans-$\eta^4$-1,3-pentadiene; (phenylamido)($\eta^5$-octahydrofluorenyl)-1,2-ethanediyltitanium s-trans-$\eta^4$-1,4-bis(trimethylsilyl)-1,3-butadiene.

(t-butylamido)(t-butyl-$\eta^5$-cyclopentadienyl)-1,2-ethanediyltitanium s-trans-$\eta^4$-1,4-dibenzyl-1,3-butadiene; (t-butylamido)($\eta^5$-indenyl)-1,2-ethanediyltitanium s-trans-$\eta^4$-2,4-hexadiene; (t-butylamido)($\eta^5$-fluorenyl)-1,2-ethanediyltitanium s-trans-$\eta^4$-3-methyl-1,3-pentadiene; (t-butylamido)($\eta^5$-fluorenyl)-1,2-ethanediyltitanium s-trans-$\eta^4$-1,3-pentadiene; (t-butylamido)($\eta^5$-fluorenyl)-1,2-ethanediyltitanium s-trans-$\eta^4$-1,4-bis(trimethylsilyl)-1,3-butadiene;

(benzylamido)($\eta^5$-octahydrofluorenyl)-1,2-ethanediyltitanium s-trans-$\eta^4$-1,4-diphenyl-1,3-butadiene, (benzylamido)($\eta^5$-indenyl)-1,2-ethanediyltitanium s-trans-$\eta^4$-1,4-dibenzyl-1,3-butadiene; (benzylamido)($\eta^5$-tetrahydroindenyl)-1,2-ethanediyltitanium s-trans-$\eta^4$-2,4-hexadiene; (benzylamido)(t-butyl-$\eta^5$-cyclopentadienyl)-1,2-ethanediyltitanium s-trans-$\eta^4$-3-methyl-1,3-pentadiene; (benzylamido)(t-butyl-$\eta^5$-cyclopentadienyl)-1,2-ethanediyltitanium s-trans-$\eta^4$-1,3-pentadiene; (benzylamido)($\eta^5$-octahydrofluorenyl)-1,2-ethanediyltitanium s-trans$\eta^4$-1,4-bis(trimethylsilyl)-1,3-butadiene;

(phenylphosphido)($\eta^5$-tetrahydroindenyl)-1,2-ethanediyltitanium s-trans-$\eta^4$-1,4-diphenyl-1,3-butadiene; (phenylphosphido)($\eta^5$-indenyl)-1,2-ethanediyltitanium s-trans-$\eta^4$-3-methyl-1,3-pentadiene; (phenylphosphido)($\eta^5$-indenyl)-1,2-ethanediyltitanium s-trans-$\eta^4$-1,3-pentadiene; (phenylphosphido)($\eta^5$-tetrahydroindenyl)-1,2-ethanediyltitanium s-trans-$\eta^4$-1,4-bis(trimethylsilyl)-1,3-butadiene;

(tert-butylamido)($\eta^5$-fluorenyl)dimethylsilanetitanium s-trans-$\eta^4$-1,4-diphenyl-1,3-butadiene; (tert-butylamido)($\eta^5$-indenyl)dimethylsilanetitanium s-trans-$\eta^4$-1,4-dibenzyl-1,3-butadiene; (tert-butylamido)($\eta^5$-indenyl)dimethylsilanetitanium s-trans-$\eta^4$-2,4-hexadiene; (tert-butylamido)($\eta^5$-tetrahydroindenyl)dimethylsilanetitanium s-trans-$\eta^4$-3-methyl-1,3-pentadiene; (tert-butylamido)($\eta^5$-tetrahydroindenyl)dimethylsilanetitanium s-trans-$\eta^4$-1,3-pentadiene; (t-butylamido)($\eta^5$-fluorenyl)-dimethylsilanetitanium s-trans-$\eta^4$-1,4-bis(trimethylsilyl)-1,3-butadiene;

(methylamido)(t-butyl-$\eta^5$-cyclopentadienyl)dimethylsilanetitanium s-trans-$\eta^4$-1,4-diphenyl-1,3-butadiene; (methylamido)($\eta^5$-indenyl)dimethylsilanetitanium s-trans-$\eta^4$-1,4-dibenzyl-1,3-butadiene; (methylamido)($\eta^5$-indenyl)dimethylsilanetitanium s-trans-$\eta^4$-2,4-hexadiene; (methylamido)($\eta^5$-fluorenyl)dimethylsilanetitanium s-trans-$\eta^4$-3-methyl-1,3-pentadiene; (methylamido)($\eta^5$-fluorenyl)dimethylsilanetitanium s-trans-$\eta^4$-1,3-pentadiene; (methylamido)(t-butyl-$\eta^5$-cyclopentadienyl)dimethylsilanetitanium s-trans-$\eta^4$-1,4-bis(trimethylsilyl)-1,3-butadiene;

(phenylamido)($\eta^5$-octahydrofluorenyl)-dimethylsilanetitanium s-trans-$\eta^4$-1,4-diphenyl-1,3-butadiene; (phenylamido)(t-butyl-$\eta^5$-cyclopentadienyl)dimethylsilanetitanium s-trans-$\eta^4$-1,4-dibenzyl-1,3-butadiene; (phenylamido)($\eta^5$-fluorenyl)dimethylsilanetitanium s-trans-$\eta^4$-2,4-hexadiene; (phenylamido)($\eta^5$-indenyl)dimethylsilanetitanium s-trans-η⁴-3-methyl- 1,3-pentadiene; (phenylamido)(η⁵-indenyl)dimethylsilanetitanium s-trans-η -1,3-pentadiene; (phenylamido)(η⁵-octahydrofluorenyl)dimethylsilanetitanium s-trans-η⁴-1,4-bis(trimethylsilyl)-1,3-butadiene; (t-butylamido)(η⁵-fluorenyl)di(trimethylsilyl)silanetitanium s-trans-η -1,4-diphenyl-1,3-butadiene; (tert-butylamido)(η⁵-tetrahydroindenyl)dimethylsilanetitanium s-trans-η⁴-1,4-dibenzyl-1,3-butadiene; (tert-butylamido)(η⁵-fluorenyl)dimethylsilanetitanium s-trans-η⁴-2,4-hexadiene; (t-butylamido)(η₅-octahydrofluorenyl)dimethylsilanetitanium s-trans-η⁴-3-methyl- 1,3-pentadiene; (t-butylamido)(η⁵-octahydrofluorenyl)dimethylsilanetitanium s-trans-η⁴-1,3-pentadiene; (t-butylamido)(η⁵-octahydrofluorenyl)dimethylsilanetitanium s-trans-η⁴-1,4-bis(trimethylsilyl)- 1,3-butadiene; (benzylamido)(η⁵-indenyl)dimethylsilanetitanium s-trans-η⁴-1,4-diphenyl- 1,3-butadiene; (benzylamido)(η⁵-fluorenyl)dimethylsilanetitanium s-trans-η ⁴-1,4-dibenzyl-1,3-butadiene; (benzylamido)(η⁵-indenyl)dimethylsilanetitanium s-trans-η⁴-2,4-hexadiene; (benzylamido)(t-butyl-η⁵-cyclopentadienyl)dimethylsilanetitanium s-trans-η⁴-3-methyl-1,3-pentadiene; (benzylamido)(t-butyl-η⁵-cyclopentadienyl)dimethylsilanetitanium s-trans-η⁴- 1,3-pentadiene; (benzylamido)(η⁵-indenyl)dimethylsilanetitanium s-trans-η⁴- 1,4-bis(trimethylsilyl)-1,3-butadiene; (phenylphosphido)(η⁵-indenyl)dimethylsilanetitanium s-trans-η⁴- 1,4-diphenyl-1,3-butadiene; (phenylphosphido)-(η⁵-octahydrofluorenyl)dimethylsilanetitanium s-trans-η⁴-1,4-dibenzyl-1,3-butadiene; (phenylphosphido)(η⁵-indenyl)dimethylsilanetitanium s-trans-η⁴-2,4-hexadiene; and (phenylphosphido)(η⁵-octahydrofluorenyl)dimethylsilanetitanium s-trans-η⁴-3-methyl-1,3-pentadiene.

The skilled artisan will recognize that additional members of the foregoing list will include the corresponding zirconium containing derivatives as well as s-cis isomeric forms of the diene ligand wherein said diene forms a π-complex as defined herein with the metal, as well as complexes that are variously substituted as herein defined.

In general, the complexes can be prepared by combining a diene compound corresponding to the group X in the resulting complex with a metal complex containing one or two leaving groups, X*, respectively (and otherwise containing the desired structure of the resulting complexes) in a suitable noninterfering, solvent at a temperature from −100° C. to 300° C., preferably from −78° to 150° C., most preferably from 0° to 125° C., contacting the mixture with a reducing agent under reducing conditions, and recovering the complex. Alternatively, the diene and reducing agent may first be contacted and the resulting mixture thereafter contacted with the metal complex under reducing conditions. By the term "reducing agent" herein is meant a metal or compound (or the product resulting from mixing a diene with such metal or compound) which, when combined with the complex causes M* or M** to be reduced from the +or +4 formal oxidation state to the +2 formal oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, and Grignard reagents. Most preferred reducing agents are the alkali metals, alkaline earth metals, and $C_1$–$C_6$ lithium alkyls, especially magnesium or lithium metals and n-butyl lithium.

Suitable reaction media for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; chlorinated-, fluorinated- or chlorofluoronated- hydrocarbons such as chlorobenzene, dichlorobenzene, and perfluorinated $C_{4-10}$ alkanes; aromatic and hydrocarbyl-substituted aromatic compounds such as benzene, toluene, xylene, and styrene, alkyl ethers having from 1 to 4 carbons in each alkyl group; $C_{1-4}$ dialkyl ether derivatives of (poly)alkylene glycols, and tetrahydrofuran. Mixtures of the foregoing are also suitable. Preferred solvents include $C_{5-10}$ alkanes and mixtures thereof.

The recovery procedure usually involves separation of the resulting alkali metal or alkaline earth metal salt and devolatilization of the reaction medium. Extraction into a secondary solvent may be employed if desired. Alternatively, if the desired product is an insoluble precipitate, filtration or other separation technique may be employed.

As previously described, the reaction may also begin with $M^{**}(X^*)_4$ or $M^*(X^*)_3$ (or solvated adducts thereof) which are contacted with a reducing agent under reducing conditions. The resulting reduced dihalide species, $MX^*_2$, or a solvated adduct thereof, is thereafter contacted with a diene compound, X, and a source of the dianion ligand: $(Z—L)^{-2}$, to form the desired metal complex which may be recovered. Examples of solvated adducts include pyridine, diethylether, tetrahydrofuran (THF), 1,2-dimethoxyethane (DME), or tetramethyl-ethylenediamine (TMEDA) containing adducts. A preferred source of the dianion ligand is the Grignard complex: $[MgCl]_2(Z—L)$, which also may be in the form of an adduct, such as: $[MgCl]_2(Z—L)(T)_t$, wherein T is a coordinating ligand group such as DME or THF, and t is a number from 0 to 5. In such a process the preferred solvent is 1,2-dimethoxyethane, diethyl ether or tetrahydrofuran.

Highly preferred diene compounds are 1,4-diphenyl-1,3-butadiene; 1,3-pentadiene; 1,4-dibenzyl-1,3-butadiene; 2,4-hexadiene; 3-methyl-1,3-pentadiene; 1,4-ditolyl-1,3-butadiene; and 1,4-bis(trimethylsilyl)-1,3-butadiene. All positional and geometric isomers of the foregoing diene reactants may be utilized.

The conjugated diene π-complexes according to the present invention are surprisingly stable and readily synthesized in high yields, contrary to expectation based on the synthesis of $Cp_2Zr$ diene complexes reported in the literature. In the latter systems, generally only synthesis and isolation at low temperatures results in the generation of π-bound diene complexes in relatively pure form.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or diisobutylalumoxane; strong Lewis acids, such as, $C_{1-30}$ hydrocarbyl substituted Group 13 compounds, especially tri(hydrocarbyl)aluminum- or tri(hydrocarbyl)boron compounds and halogenated derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, inert, compatible, noncoordinating, ion forming compounds (including the use of such compounds under oxidizing conditions); bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718), EP-A-520,732 (equivalent to U.S. Ser. No. 07/876,268), and WO/US 93/23412 (equivalent to U.S. Ser. Nos. 07/884,966 filed May 1, 1992, now U.S. Pat. No. 5,350,723), the teachings of which are hereby incorporated by reference.

Combinations of strong Lewis acids, especially the combination of a trialkyl aluminum compound having from 1 to 4 carbons in each alkyl group and a halogenated tri(hydrocarbyl)boron compound having from 1 to 10 carbons in each hydrocarbyl group, especially tris(pentafluorophenyl)borane, further combinations of such strong Lewis acid mixtures with a polymeric or oligomeric alumoxane, and combinations of a single strong Lewis acid, especially tris(pentafluorophenyl)borane with a polymeric or oligomeric alumoxane are especially desirable activating cocatalysts.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0° to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), DME, and mixtures thereof.

The electrolysis may be conducted in a standard electrolytic cell containing an anode and cathode (also referred to as the working electrode and counter electrode respectively). Suitably materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, A−. Preferred supporting electrolytes are salts corresponding to the formula G+A−; wherein:

G+ is a cation which is nonreactive towards the starting and resulting complex, and A− is a noncoordinating, compatible anion.

Examples of cations, G+, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and A− migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoro-aryl) borates having from 1 to 10 carbons in each hydrocarbyl group, especially tetra-n-butylammonium tetrakis(pentafluorophenyl) borate.

Suitable ion forming compounds useful as a cocatalyst in one embodiment of the present invention comprise a cation which is a Bronsted acid capable of donating a proton, and an inert, compatible, noncoordinating, anion, A−. Preferred anions are those containing a single coordination complex comprising a charge-bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

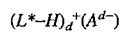

wherein:

L* is a neutral Lewis base;

(L*−H)$^+$ is a Bronsted acid;

$A^{d-}$ is a noncoordinating, compatible anion having a charge of d−, and d is an integer from 1 to 3.

More preferably $A^{d-}$ corresponds to the formula: $[M'^k+ Q_n]^{d-}$ wherein:

k is an integer from 1 to 3;

n is an integer from 2 to 6;

n−k=d;

M' is an element selected from Group 13 of the Periodic Table of the Elements; and Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide.

In a more preferred embodiment, d is one, i.e. the counter ion has a single negative charge and corresponds to the formula A−. Activating cocatalysts comprising boron which are particularly useful in the preparation of catalysts of this invention may be represented by the following general formula:

[L*−H]+[BQ$_4$]− wherein:

L* is as previously defined;

B is boron in a valence state of 3; and

Q is a fluorinated $C_{1-20}$ hydrocarbyl group.

Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:

trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(sec-butyl)ammonium tetrakis(pentafluorophenyl) borate, N,N-dimethylanilinium tetrakis(pentafluorophenyl) borate, N,N-diethylanilinium tetrakis(pentafluorophenyl) borate, N,N-dimethyl-(2,4,6-trimethylanilinium) tetrakis(pentafluorophenyl) borate, trimethylammonium tetrakis-(2,3,4,6-tetrafluorophenylborate, triethylammonium tetrakis-(2,3,4,6-tetrafluorophenyl) borate, tripropylammonium tetrakis-(2,3,4,6-tetrafluorophenyl) borate, tri(n-butyl)ammonium tetrakis-(2,3,4,6-tetrafluorophenyl) borate, dimethyl(t-butyl)ammonium tetrakis-(2,3,4,6-tetrafluorophenyl) borate, N,N-dimethylanilinium tetrakis-(2,3,4,6-tetrafluorophenyl) borate, N,N-diethylanilinium tetrakis-(2,3,4,6-tetrafluorophenyl) borate, and N,N-dimethyl-(2,4,6-trimethylanilinium) tetrakis-(2,3,4,6-tetrafluorophenyl) borate;

dialkyl ammonium salts such as:

di-(i-propyl)ammonium tetrakis(pentafluorophenyl) borate, and dicyclohexylammonium tetrakis(pentafluorophenyl) borate;

and tri-substituted phosphonium salts such as:

triphenylphosphonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate.

Preferred [L*−H]+ cations are N,N-dimethylanilinium and tributylammonium.

Another suitable ion forming, activating cocatalyst comprises a salt of a cationic oxidizing agent and a noncoordinating, compatible anion represented by the formula:

$(Ox^{e+})_d(A^{d-})_e$ wherein:

$Ox^{e+}$ is a cationic oxidizing agent having a charge of e+;

e is an integer from 1 to 3; and $A^{d-}$, and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

©+A− wherein:

©+ is a $C_{1-20}$ carbenium ion; and

A− is as previously defined. A preferred carbenium ion is the trityl cation, i.e. triphenylcarbenium.

The foregoing activating technique and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

The molar ratio of catalyst/cocatalyst employed preferably ranges from 1:10,000 to 100:1, more preferably from 1:5000 to 10:1, most preferably from 1:10 to 1:1. In a particularly preferred embodiment of the invention the cocatalyst can be used in combination with a tri(hydrocarbyl)aluminum compound having from 1 to 10 carbons in each hydrocarbyl group or an oligomeric or polymeric alumoxane. Mixtures of activating cocatalysts may also be employed. It is possible to employ these aluminum compounds for their beneficial ability to scavenge impurities such as oxygen, water, and aldehydes from the polymerization mixture. Preferred aluminum compounds include trialkyl aluminum compounds having from 2 to 6 carbons in each alkyl group, especially those wherein the alkyl groups are ethyl, propyl, isopropyl, n-butyl, isobutyl, pentyl, neopentyl, or isopentyl, and methylalumoxane, modified methylalumoxane (that is, methylalumoxane modified by reaction with triisobutyl aluminum) (MMAO) and diisobutylalumoxane. The molar ratio of aluminum compound to metal complex is preferably from 1:10,000 to 1000:1, more preferably from 1:5000 to 100:1, most preferably from 1:100 to 100:1. A most preferred activating cocatalyst comprises both a strong Lewis acid and an alumoxane, especially tris(pentafluorophenyl)borane and methylalumoxane, modified methylalumoxane, or diisobutylalumoxane.

The catalysts may be used to polymerize ethylenically and/or acetylenically unsaturated monomers having from 2 to 100 carbon atoms either alone or in combination. Preferred monomers include the $C_{2-20}$ α-olefins especially ethylene, propylene, isobutylene, 1-butene, 1-hexene, 4-methyl-1-pentene, and 1-octene and mixtures thereof. Other preferred monomers include styrene, $C_{1-4}$ alkyl substituted styrene, tetrafluoroethylene, vinylbenzocyclobutane, ethylidenenorbornene and 1,4-hexadiene.

In general, the polymerization may be accomplished at conditions well known in the prior art for Ziegler-Natta or Kaminsky-Sinn type polymerization reactions, i.e., temperatures from 0°–250° C. and pressures from atmospheric to 1000 atmospheres (0.1 to 100 MPa). Suspension, solution, slurry, gas phase or other process conditions may be employed if desired. A support, especially silica, modified silica (silica modified by calcining, treatment with a trialkylaluminum compound having from 1 to 10 carbons in each alkyl group, or treatment with an alkylalumoxane), alumina, or a polymer (especially polytetrafluoroethylene or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}:1$ to $10^{-1}:1$, more preferably from $10^{-12}:1$ to $10^{-5}:1$.

Suitable solvents for polymerization are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), 4-vinylcyclohexene, and vinylcyclohexane. Mixtures of the foregoing are also suitable.

The catalysts may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, abandoned, as well as U.S. Ser. No. 08/10958, pending, filed Jan. 29, 1993, the teachings or which are hereby incorporated by reference herein.

One such solution phase polymerization process comprises:

contacting in a solvent one or more α-olefins with a metal complex according to the present invention and one or more cocatalyst activators in one or more continuous stirred tank or tubular reactors connected in series or parallel, and recovering the resulting polymerizate.

In another such solution phase polymerization process, in one or more of the foregoing reactors, one or more α-olefins are also contacted with a catalyst composition comprising one or more metal complexes according to the present invention in admixture with one or more homogeneous metallocene complexes other than a complex according to the present invention, said catalyst composition also comprising one or more cocatalyst activators.

In yet another solution process an ethylene/α-olefin interpolymer composition is prepared by:

(A) contacting ethylene and at least one other α-olefin under solution polymerization conditions in the presence of a homogeneous catalyst composition comprising a metal complex of the present invention with at least one of the aforementioned activating cocatalysts in at least one reactor to produce a solution of a first interpolymer, (B) contacting ethylene and at least one other α-olefin under solution polymerization conditions and at a higher polymerization reaction temperature than used in step (A) in the presence of a heterogeneous Ziegler catalyst in at least one other reactor to produce a solution of a second interpolymer, and (C) combining the solution of the first interpolymer with the solution of the second interpolymer to form a solution comprising the ethylene/α-olefin interpolymer composition, and (D) recovering the ethylene/α-olefin interpolymer composition.

Preferably the heterogeneous Ziegler catalyst comprises:

(i) a solid support component comprising magnesium halide, silica, modified silica, alumina, aluminum phosphate, or a mixture thereof, and (ii) a transition metal component represented by the formula:

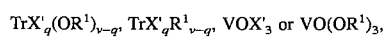

wherein:

Tr is a Group 4, 5, or 6 metal, q is a number from 0 to 6 that is less than or equal to v, v is the formal oxidation number of Tr, X' is a halogen, $R^1$ independently each occurrence is a hydrocarbyl group having from 1 to 20 carbon atoms.

These polymerizations are generally carried out under solution conditions to facilitate the intimate mixing of the two polymer-containing streams. The foregoing technique allows for the preparation of ethylene/α-olefin interpolymer compositions having a broad range of molecular weight distribution and composition distribution. Preferably, the heterogeneous catalyst is also chosen from those catalysts which are capable of efficiently is producing the polymers under high temperature, especially, temperatures greater than or equal to 180° C. under solution process conditions.

In a still further embodiment, there is provided a process for preparing an ethylene/α-olefin interpolymer composition, comprising:

(A) polymerizing ethylene and at least one other α-olefin in a solution process under suitable solution polymerization temperatures and pressures in at least one reactor containing a catalyst composition comprising the metal complex of the present invention with at least one of the aforementioned activating cocatalysts to produce a first interpolymer solution, (B) passing the interpolymer solution of (A) into at least one other reactor containing a heterogeneous Ziegler catalyst, in the presence of ethylene and optionally one other α-olefin under solution polymerization conditions to form a solution comprising the ethylene/α-olefin interpolymer composition, and (C) recovering the ethylene/α-olefin interpolymer composition.

Preferably the heterogeneous Ziegler catalyst comprises:

(i) a solid support component comprising a magnesium halide or silica, and (ii) a transition metal component represented by the formula:

$$TrX'_q(OR^1)_{v-q}, TrX'_qR^1_{v-q}, VOX'_3 \text{ or } VO(OR^1)_3,$$

wherein:

Tr, X', q, v, and $R^1$ are as previously defined.

The foregoing technique also allows for the preparation of ethylene/α-olefin interpolymer compositions having a broad range of molecular weight distributions and composition distributions. Particularly desirable α-olefins for use in the foregoing processes are $C_{4-8}$ α-olefins, most desirably 1-octene.

Having described the invention the following examples are provided as further illustration thereof and are not to be construed as limiting. Unless stated to the contrary all parts and percentages are expressed on a weight basis.

EXAMPLES 1–15

Catalyst Preparations A1–A9

(A) Preparation of (t-butylamido)(tetramethyl-$\eta^5$-cyclopentadienyl)dimethylsilanetitanium-$\eta^4$-1,4-trans, trans-diphenyl-1,3-butadiene 1. Ti(IV) dihalide With Lithium Reductant In an inert atmosphere glove box, 2.211 g (0.0060 mol) of $C_5Me_4SiMe_2NCMe_3TiCl_2$ ((t-butylamido)-(tetramethyl-$\eta$ 5-cyclopentadienyl)dimethylsilanetitanium dichloride) was dissolved into 150 mL of diethyl ether. To this solution was added 1.238 g (0.0060 mol) of 1,4-trans, trans-diphenyl-1,3-butadiene, using 15 mL of diethyl ether to wash the solid into the flask. This was followed by addition of 0.126 g (0.018 mol) of lithium metal using 10 mL of diethyl ether to wash the metal into the flask. The lithium metal used was a high sodium content lithium powder (Na content≧0.5 mol percent). The color changed from yellow to green within minutes and within 30 minutes changed again to a deep purple color. The total reaction time was 3.5 hours. The solvent was removed under reduced pressure, the solid residue was extracted with pentane (8×60 mL) and filtered. The filtrate was combined and the pentane removed under reduced pressure. The solid was collected giving 2.050 g (67.8 percent yield) of (t-butylamido)-(tetramethyl-$\eta^5$-cyclopentadienyl)dimethyl-silanetitanium s-trans-$\eta^4$-1,4-trans, trans-diphenyl- 1,3-butadiene (Formula A).

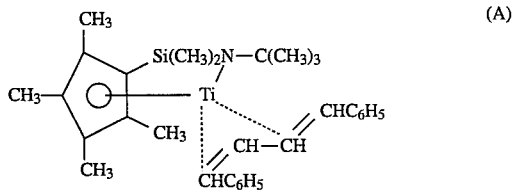

(A)

The product's identity was confirmed by $^1H$ NMR spectral analysis. Characterization for (t-butylamido)(tetramethyl-$\eta^5$-cyclopentadienyl)dimethyl-silanetitanium s-trans-$\eta^4$-1,4-trans, trans-diphenyl-1,3-butadiene ($C_6D_6$): δ7.28–7.17 (m, $C_6H_5$); 6.94 (m, $C_6H_5$, 1H); 4.62, 4.06(multiplets, PhCHCHCHCHPh, 2H each); 1.62, 1.25 (s, $C_5Me_4$, 6H each); 1.35 (s, N-tert-Bu, 9H); 0.60 (s, $SiMe_2$, 6H). The spectrum is illustrated in FIG. 1.

The mass spectrum characterization (negative ion) gave a single peak at m/z of 503 corresponding to the molecular ion of (t-butylamido)(tetramethyl-$\eta$ $^5$-cyclopentadienyl)dimethylsilanetitanium-$\eta^4$-1,4-trans, trans-diphenyl-1,3-butadiene.

2. Ti(IV) Dihalide With Grignard Reductant

In an inert atmosphere glove box, 0.500 g (0.0014 mol) of $C_5Me_4SiMe_2NCMe_3TiCl_2$ ((t-butylamido)-(tetramethyl-$\eta$ 5-cyclopentadienyl)dimethylsilanetitanium dichloride) was dissolved into 40 mL of diethyl ether. To this solution was added 0.56 g (0.0027 mol) of 1,4-trans, trans-diphenyl-1,3-butadiene followed by addition of 2.4 mL of a 2.3M diethyl ether solution of isopropylmagnesium chloride (0.0055 mol). The color changed from yellow to orange within minutes and within 30 minutes changed again to a deep purple color. The total reaction time was 1.5 hours. The solvent was removed under reduced pressure, the solid residue was extracted with pentane (5×15 mL) and filtered. The filtrate was combined and the pentane removed under reduced pressure. The solid was collected on a frit and washed further with cold (−34° C.) pentane. Removing the pentane under reduced pressure gave 0.377 grams of a solid. Proton NMR analysis indicated this product was (t-butylamido)(tetramethyl-$\eta^5$-cyclopentadienyl)dimethylsilanetitanium s-trans-$\eta^4$-1,4-trans, trans-diphenyl-1,3-butadiene containing approximately 25–50 mol percent uncomplexed diene.

3. Ti(III) Monohalide with Lithium Reductant

In an inert atmosphere glove box, 1.240 g (0.0027 mol) of $[MgCl]_2[C_5Me_4SiMe_2NCMe_3](EtO_2)_x$ (the diether adduct of the diGrignard of (tetramethyl-$\eta^5$-cyclopentadienyl)dimethylsilane(t-butylamine), titrated molecular weight 459.5 g/mol) was added to a slurry of $TiCl_3(THF)_3$ (1.000 g, 0.0027 mol) in 50 mL of tetrahydrofuran (THF). An additional quantity of THF (10 mL) was used to wash the ligand salt into the flask. After 5 minutes stirring time the diene, 1,4-trans, trans-diphenyl-1,3-butadiene (0.5567 g 0.0027 mol) was added followed by addition of (0.020 g, 0.0029 mol) of lithium metal. After 2 hours reaction time the THF was removed under reduced pressure, the solid residue was extracted with pentane (6×15 mL), and filtered. The combined filtrate was dried under reduced pressure leaving a sticky purple solid which was identified by proton NMR analysis as (t-butylamido)(tetramethyl-$\eta$ $^5$-cyclopentadienyl)dimethylsilanetitanium s-trans-$\eta$ $^4$-1,4-trans, trans-diphenyl-1,3-butadiene.

4. $TiCl_4$ with Magnesium Reductant

In an inert atmosphere glove box, 0.500 g (0.0015 mol) of $TiCl_4(THF)_2$ was loaded into a 250 mL glass flask and slurried into 80 mL of DME. To this was added magnesium powder (0.146 g, 6.01 mmol) using 10 mL DME to aid in the transfer of the solid reductant. The reaction mixture was refluxed. After 1 to 1.5 hours an additional 0.146 g of magnesium was added to the reaction. Total reflux time was approximately 3 to 3.5 hr. The reaction mixture was cooled and 0.309 g, 1.50 mmol, of 1,4-trans, trans-diphenyl-1,3-butadiene was added followed by addition of the ligand, $[MgCl]_2[C_5Me_4SiMe_2NCMe_3](DME)$ (0.957 g, 1.5 mmol), again using 10 mL of fresh DME to aid in each of the transfers. After stirring at room temperature for 30 minutes, the reaction mixture was filtered and the filtrate was taken to dryness under reduced pressure. The product was extracted with hexane (3×50 mL) and then filtered. The combined filtrate was taken to dryness under reduced pressure to give the product, (t-butylamido)(tetramethyl-$\eta^5$-cyclopentadienyl)dimethylsilanetitanium s-trans-$\eta^4$-1,4-trans, trans-diphenyl- 1,3-butadiene, as a purple solid which was identified by proton NMR analysis. Yield of the product (including residual quantities of uncomplexed diene) was 0.479 g (63.5 percent).

5. TiCl$_3$ with Magnesium Reductant

A flask was charged with 1.000 g (2.70 mmol) of TiCl$_3$(THF)$_3$, 200 mL THF and 0.13 g (5.35 mmol) of magnesium turnings. The reaction mixture was stirred overnight. To the resulting black solution was added 0.557 g (2.70 mmol) of 1,4-trans, trans-diphenyl-1,3-butadiene. Over a period of about 5 minutes, 1.396 g (2.70 mmol) of (MgCl)$_2$(C$_5$Me$_4$SiMe$_2$NCMe$_3$)(EtO$_2$)$_2$ was added as a solid. The reaction mixture was stirred overnight, then filtered. The solvent was removed under reduced pressure and the residue was extracted with toluene and filtered. The solvent was removed to give a slightly sticky product. It was extracted with hexane and then filtered. The filtrate was concentrated until a solid began to form. The slurry was chilled overnight in a freezer (−40° C.). The purple product was collected on a frit, washed with cold hexane and dried under reduced pressure. Additional product was isolated from the filtrate in a similar fashion after concentrating it until solid began to form. Total yield was 0.52 g, 38.2 percent. The product, (t-butylamido)(tetramethyl-$\eta^5$-cyclopentadienyl)dimethylsilanetitanium s-trans-$\eta^4$-1,4-trans, trans-diphenyl- 1,3-butadiene, was identified by proton NMR analysis.

6. Ti(IV) Dihalide with Organolithium Reductant

In an inert atmosphere glove box, 0.400 g (0.002 mol) of 1,4-trans, trans-diphenyl-1,3-butadiene and 0.750 g (0.002 mol) of C$_5$Me$_4$SiMe$_2$NCMe$_3$TiCl$_2$ ((t-butylamido)-(tetramethyl-$\eta^5$-cyclopentadienyl)dimethylsilanetitanium dichloride) were dissolved/suspended in 100 mL of anhydrous hexane. To this was added 0.004 mol n-butyl lithium (2.1 mL×1.89M in hexane by titration, available from Aldrich Chemical Co.). The color immediately darkened. The mixture was heated to reflux with stirring. After one hour the mixture was filtered through a medium porosity fritted funnel using Celite™ diatomaceous earth filter aid, and the remaining solids were washed with approximately 30 mL of additional hexane. The deeply colored solutions were combined and the hexane evaporated under reduced pressure to leave a deep purple solid (0.81 g). Proton NMR analysis indicated this product was highly pure (t-butylamido)(tetramethyl-$\eta^5$-cyclopentadienyl)dimethylsilanetitanium s-trans-$\eta^4$-1,4-trans, trans-diphenyldiphenyl- 1,3-butadiene.

7. Ti(IV) Dihalide with KC$_8$ as the Reductant

In an inert atmosphere glove box, 100 mg (0.272 mmol) of (C$_5$Me$_4$SiMe$_2$N$^t$Bu)TiCl$_2$ and 56 mg (0.27 mmol) of 1,4-trans, trans-diphenyl- 1,3-butadiene was dissolved in 30 mL of diethyl ether. To this solution was added 0.1 g (0.7 mmol) of KC$_8$ (potassium graphite). The mixture darkened gradually. After stirring overnight, the mixture was filtered. The purple filtrate was concentrated under reduced pressure to give a solid residue. The residue was extracted with hexanes. The hexanes extract was filtered and the solvent was removed from the filtrate under reduced pressure to give a solid residue. The product, (C$_5$Me$_4$SiMe$_2$N$^t$Bu)Ti(s-trans-$\eta^4$-1,4-trans, trans-diphenyl-1,3-butadiene) was identified by its $^1$H NMR spectrum. The NMR analysis showed that the product contained about 55 mole percent uncomplexed diene.

8. Ti(IV) Dihalide with Magnesium Reductant

In an inert atmosphere glove box 0.200 g (0.543 mmol) of (C$_5$Me$_4$SiMe$_2$N$^t$Bu)TiCl$_2$ was dissolved into 20 mL of THF. To this solution was added 0.112 g (0.543 mmol) of 1,4-trans, trans-diphenyl-1,3-butadiene and 26 mg (1.1 mmol) Mg metal. Each addition was aided by using 10 mL fresh THF to wash the reagents into the flask. The reaction mixture was stirred overnight at room temperature, after which time the color of the solution was reddish purple. The THF was removed under reduced pressure and the product was extracted with pentane until the filtrate was colorless. The filtrate was taken to dryness giving the product as a slightly sticky purple solid. The product, (C$_5$Me$_4$SiMe$_2$N$^t$Bu)Ti(s-trans-$\eta^4$-1,4-trans, trans-diphenyl-1,3-butadiene), was identified by its $^1$H NMR spectrum.

9. Ti(IV) Dihalide with t-Butyl Lithium Reductant

In the drybox, 0.28 g of trans, trans-1,4-diphenyl-1,3-butadiene was dissolved/suspended in 20 mL of anhydrous pentane. To this was added 1.68 mL of $^t$BuLi (about 1.7M) in pentane. The mixture turned yellow/orange and became cloudy immediately. After 30 minutes of stirring, 0.50 g of [(Me$_4$C$_5$)SiMe$_2$N$^t$Bu]TiCl$_2$ was added using about 10 mL of pentane to wash the solid into the flask. The color immediately turned deep red/purple. The mixture was stirred for one hour, then filtered through a medium porosity fritted funnel. The volatile materials were evaporated under reduced pressure to leave a deep purple oily material. $^1$H NMR analysis of this material indicated that it contained the desired product. The material was purified by washing with a minimal amount of hexane, yielding a purple powder. The $^1$H NMR spectrum of this powder was consistent with that of [(Me$_4$C$_5$)SiMe$_2$N$^t$Bu]Ti(s-trans-$\eta^4$-1,4-trans- trans-diphenyl-1,3-butadiene).

B) Preparation of Active Catalyst B1–B2

1. In an inert atmosphere glove box, 0.050 g (0.099 mol) of (t-butylamido)(tetramethyl-$\eta^5$-cyclopentadienyl)dimethylsilanetitanium s-trans-$\eta^4$-1,4-trans, trans-diphenyl-1,3-butadiene was dissolved in 20 mL of toluene followed by addition of 0.0795 g (0.099 mmol) of dimethylanilinium tetrakis(pentafluorophenyl) borate using 10 mL of toluene to wash the solids into the reaction flask. Within 10 to 15 minutes the color had turned to orange color. After one hour the solvent was removed under reduced pressure. The product was washed with pentane (3×10 mL with drying between each wash). The product was a dark yellow solid.

2. A standard H-cell for electrolysis comprising two electrode wells separated by a fine glass frit, platinum mesh working and counter electrodes, and a silver reference electrode was placed inside an inert atmosphere glove box filled with argon. Each half of the cell was filled with 1,2-difluorobenzene solvent (5 mL in the working compartment, 4 mL in the counter compartment) and tetra-n-butylammonium tetrakis(pentafluorophenyl) borate supporting electrolyte (8 mmole). The complex, (t-butylamido)(tetramethyl-$\eta^5$-cyclopentadienyl)dimethylsilanetitanium s-trans-$\eta^4$-1,4-diphenyl-1,3-butadiene (0.024 g) was placed in the working compartment. A sweep of the working electrode potential was used to determine the voltage to be applied during electrolysis. The solution was stirred and the potential was stepped to the first oxidation wave of the complex and adjusted to obtain a 1.5 mA current. The applied potential was turned off when the current dropped to 30 percent of its original value having passed a total of 3.3 coulombs. This represents a conversion of 72 percent. The working compartment solution was then pipetted into a round bottom flask and the solvent was removed under vacuum. The resulting solid product was extracted with toluene (2.0 mL) and used directly in the polymerization reaction.

C) Polymerization Examples 1–15

A 2 L stirred reactor was charged with the desired amounts of mixed alkane solvent (Isopar™ E, available from Exxon Chemicals Inc.) and 1-octene comonomer. Trialkylaluminum additive, if used, was also added at this time. Hydrogen was added as a molecular weight control agent by differential pressure expansion from an approximately 75 mL addition tank at 2070 kPa. The reactor was heated to the polymerization temperature and saturated with is ethylene at 3450 Kpa. Catalyst/cocatalyst solutions were prepared in a drybox by syringing the desired amount of 0.0050M metal complex solution (in toluene) into a solution of the cocatalyst in toluene in the desired molar ratio. This solution was then transferred to a catalyst addition tank and injected into the reactor. The polymerization was allowed to proceed for the desired time with ethylene on demand. Where indicated multiple additions of catalyst/cocatalyst mixture were added during the course of the polymerization. After 15 minutes run time, the solution was removed from the reactor and quenched with isopropanol. A hindered phenol anti-oxidant (Irganox™ 1010, available from Ciba Geigy Corp.) was added to the polymer solution. The polymers were dried in a vacuum oven set at 120° C. for about 20 hours. Results are contained in Table I.

DME to aid in the transfer. After stirring at room temperature for 30 minutes, the reaction mixture was filtered and the filtrate was taken to dryness under reduced pressure. The product was extracted with hexane (3×30 mL) and then filtered. The combined filtrate was taken to dryness under reduced pressure to give the product, (t-butylamido)(tetramethyl-$\eta^5$-cyclopentadienyl)dimethylsilanetitanium $\eta^4$-3-methyl-1,3-pentadiene, as a dark reddish oil. Yield of the product was 0.410 g (72 percent). Proton NMR characterization ($C_6D_6$, RT): δ3.71 (pseudo t, CHHCHCMeCHMe, 1H, J=11 Hz); 2.84 (overlapping dd, CHHCHCMeCHMe, 1H, J=7.4, 8.8 Hz); 2.18, 2.07 (s, $C_5Me_4$, 3H each); 1.9 (q, CHHCHCMeCHMe, 1H, J=5.5 Hz); 1.81 (d, CHHCHCMeCHMe, 3H, J=5.4 Hz); 1.78 (m, CHHCHCMeCHMe, 1H); 1.60 (s, CHHCHCMeCHMe, 3H); 1.27, 1.24 (s, $C_5Me_4$, 3H each); 1.18 (s, t-Bu, 9H); 0.76, 0.75 (s, $SiMe_2$, 6H).

EXAMPLE 17

Synthesis of
($C_5Me_4SiMe_2N^tBu$)Ti($\eta^4$-1,3-pentadiene)

In an inert atmosphere glove box 0.500 g (1.36 mmol) of ($C_5Me_4SiMe_2N^tBu$)TiCl$_2$ was dissolved into approximately 50 mL of dry, degassed hexane. To this yellow solution was added 2.70 mL of tech. grade piperylene (27.1 mmol)

TABLE I

| Ex. | Cat. Prep. | Amt. μmol | Co-catalyst | Amt. μmol | Additive | Amt. μmol | Temp. °C. | ΔH$_2$ kPa | Solvent (g) | 1-Octene (g) | Polymer (g) | Efficiency (Kg/g Ti) |
|---|---|---|---|---|---|---|---|---|---|---|---|---|
| 1 | A-2 | 1.0 | TPFB$^1$ | 1.0 | — | — | 140 | 179 | 740 | 119 | 30.0 | 626 |
| 2 | A-1 | 1.0 | " | 1.0 | — | — | " | 186 | 744 | " | 41.9 | 875 |
| 3 | " | 3.0 | " | 3.0 | — | — | 180 | 193 | 659 | 204 | 14.8 | 103 |
| 4 | " | 0.5 | ATPFB$^2$ | 0.5 | — | — | 140 | 172 | 741 | 134 | 8.3 | 346 |
| 5 | " | 1.0 | IBA$^3$ | 20 | — | — | " | 172 | " | 122 | 3.1 | 65 |
| 6 | " | 2.0 | TPFB$^1$ | 2.0 | TIBA$^4$ | 20 | " | 179 | " | 122 | 42.0 | 438 |
| 7 | " | 1.0 | B-1* | — | — | — | " | " | " | 115 | 54.6 | 1,140 |
| 8 | " | 1.0 | B-2* | — | — | — | " | " | " | 119 | 32.9 | 687 |
| 9 | " | 1.5 | B-1* | — | — | — | 180 | " | 659 | 200 | 16.0 | 223 |
| 10 | " | 4 × 0.5 | TPFB$^1$ | 4 × 0.5 | TIBA$^4$ | 20 | " | 172 | 815 | 52 | 31.4 | 328 |
| 11 | " | 4 × 0.5 | B-1* | — | " | " | " | 179 | 811 | 52 | 43.1 | 450 |
| 12 | " | 0.15 | " | — | — | — | 100 | 172 | 666 | 196 | 57.5 | 8,000 |
| 13 | " | " | " | — | TIBA$^4$ | 20 | " | 207 | 659 | 201 | 113.0 | 15,700 |
| 14 | " | 0.10 | " | — | " | 15 | 60 | 345 | 607 | 260 | 82.0 | 17,100 |
| 15 | " | 0.25 | " | — | TEA$^5$ | 10 | 140 | 179 | 741 | 122 | 19.8 | 1,650 |

$^1$trispentafluorophenylborane, B($C_6F_5$)$_3$
$^2$dimethylanilinium tetrakisperfluorophenylborate, ($Me_2NC_6H_5$) + ($C_6F_5$)$_4$B—
$^3$diisobutylalumoxane
$^4$triisobutylaluminum
$^5$triethylaluminum
*following the activated catalyst preparation methods B-1, and B-2

EXAMPLE 16

Figure 2:
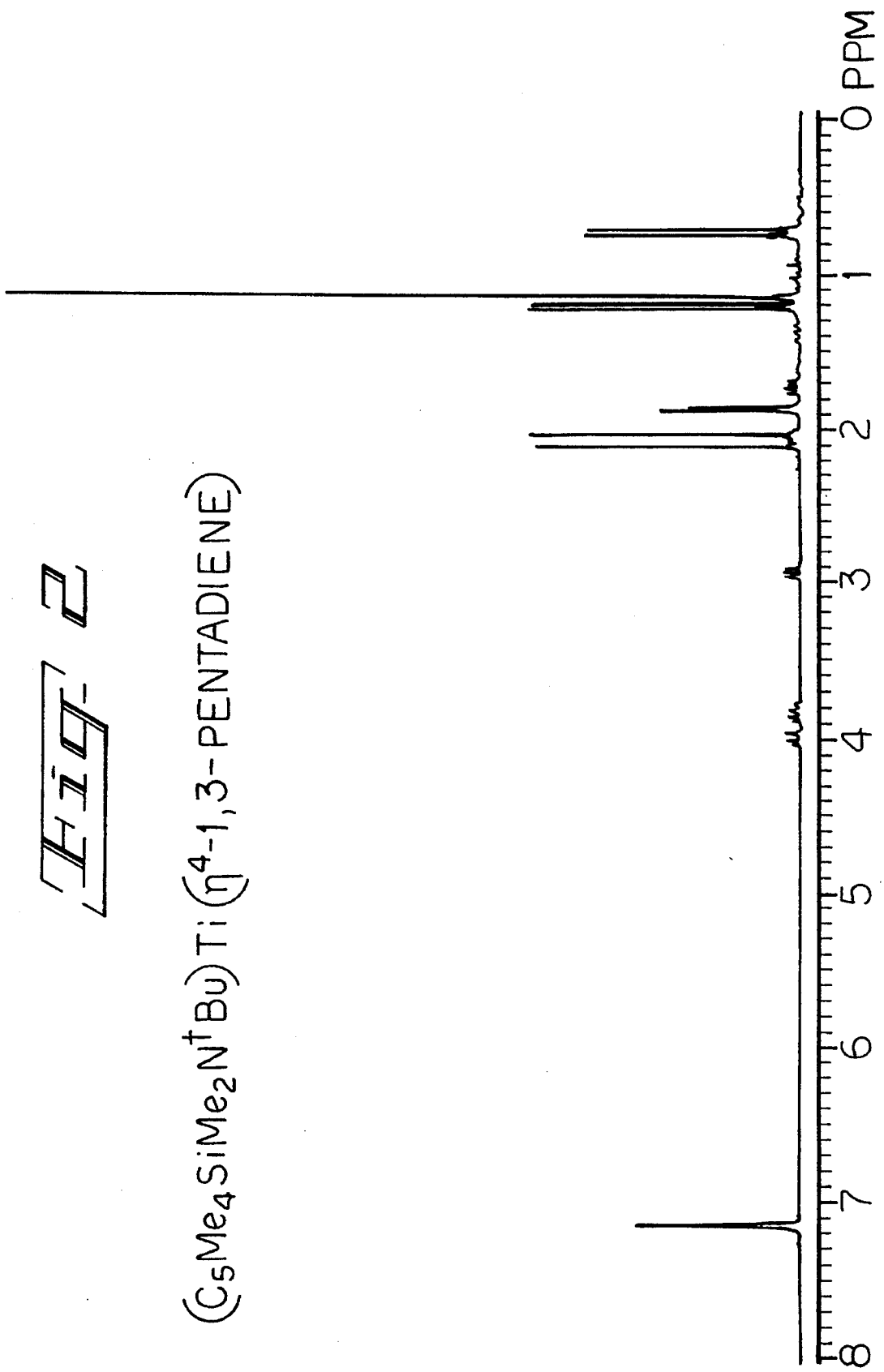

Preparation of
(t-butylamido)(tetramethyl-$\eta^5$-cyclopentadienyl)
dimethylsilanetitanium $\eta^4$-3-methyl-1,3-pentadiene In an inert atmosphere glove box, 0.500 g (0.0015 mol) of TiCl$_4$(THF)$_2$ was loaded into a 100 mL glass flask and slurried into 40 mL of dimethoxyethane (DME). To this was added magnesium powder (0.146 g, 6.01 mmol) using 10 mL DME to aid in the transfer of the solid reductant. The reaction mixture was refluxed for approximately 3 to 3.5 hours. The reaction mixture was cooled and 1.68 mL (14.9 mmol) of 3-methyl-1,3-pentadiene was added followed by addition of the ligand, [MgCl]$_2$[$C_5Me_4SiMe_2NCMe_3$] (DME) (0.957 g, 1.5 mmol), again using 10 mL of fresh followed by 1.09 mL of $^n$BuLi (2.72 mmol, 2.5M in mixed hexanes). Addition of the latter resulted in an immediate color change to a dark reddish color. The reaction mixture was refluxed for 45 to 60 minutes after which time the reaction mixture was cooled to room temperature. The hexane solution was filtered through Celite™ brand filtering aid, using 10 mL of additional hexane to wash the insolubles. The combined hexane filtrate was taken to dryness under reduced pressure giving the product, ($C_5Me_4SiMe_2N^tBu$)-Ti($\eta^4$-1,3-pentadiene), as a very dark reddish purple solid in 96.5 percent yield (0.97 g). NMR characterization: $^1$H NMR ($C_6D_6$, ppm, approximate coupling constants were determined with the aid of simulation): δ 4.01 (overlapping dd, CHH=CH—CH=CHCH$_3$, 1H, J$_{HH}$=9.5, 7.3 Hz); 3.84 (overlapping ddd, CHH=CH—CH=CHCH$_3$, 1H, J$_{HH}$=13.3, 9.5, 9 Hz); 2.97 (overlapping dd, CHH=CH—CH=CHCH$_3$, 1H, J$_{HH}$=9, 8 Hz); 2.13 (s, C$_5$Me$_4$, 3H); 2.1 (multiplet, partly overlapped by two singlets, CHH=CH—CH=CHCH$_3$, 1H, J$_{HH}$=8, 5.5 Hz); 2.05 (s, C$_5$Me$_4$, 3H); 1.88 (d, CHH=CH—CH=CHCH$_3$, 3H, J$_{HH}$=5.5); 1.75 (dd, CHH=CH—CH=CHCH$_3$, 1H, J$_{HH}$= 13.3, 7.3 Hz); 1.23, 1.21 (s each, C$_5$Me$_4$, 3H each); 1.16(s, $^t$Bu, 9H); 0.76, 0.73 (s each, SiMe$_2$, 3H each). The spectrum is illustrated in FIG. 2.

EXAMPLE 18

Synthesis of (C$_5$Me$_4$SiMe$_2$N$^t$Bu)Ti(s-cis-$\eta^4$-2,4-hexadiene)

Figure 3:
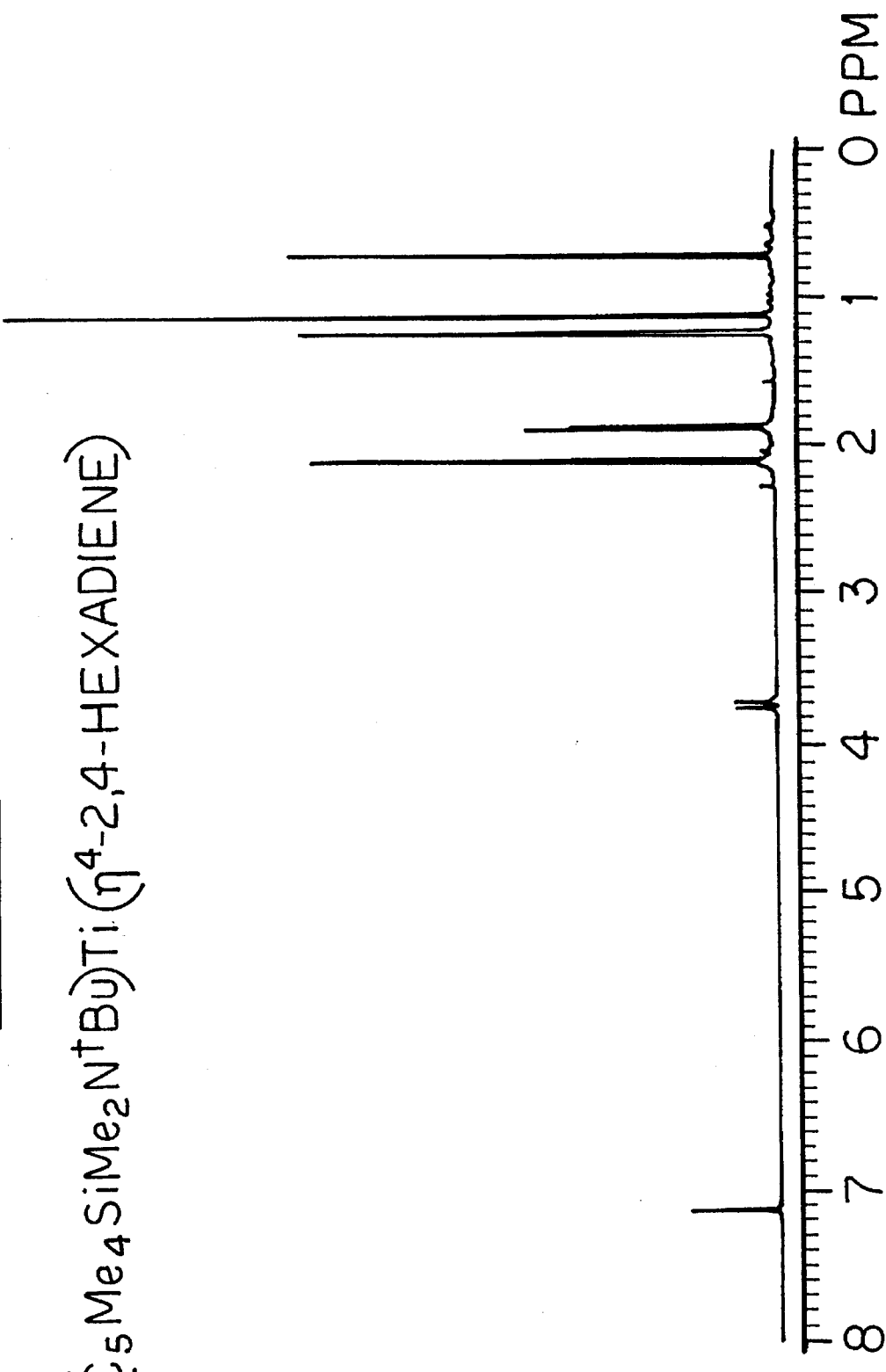

In an inert atmosphere glove box 0.500 g (1.36 mmol) of (C$_5$Me$_4$SiMe$_2$N$^t$Bu)TiCl$_2$ was dissolved into approximately 50 mL of dry, degassed hexane. To this yellow solution was added 1.55 mL of 2,4-hexadiene (mixture of isomers, 13.6 mmol) followed by 1.09 mL of n-butyllithium (2.72 mmol, 2.5M in hexanes). Addition of the latter resulted in an immediate color change to a dark reddish color. The reaction mixture was refluxed for 45 to 60 minutes after which time the reaction mixture was cooled to room temperature. The hexane solution was filtered through Celite™, using 10 mL of additional hexane to wash the insolubles. The combined hexane filtrate was taken to dryness under reduced pressure giving the crude product, (C$_5$Me$_4$SiMe$_2$N$^t$Bu)Ti(s-cis-$\eta^4$-2,4-hexadiene), as a very dark reddish purple solid in 97.4 percent yield (0.502 g). Further purification was accomplished by recrystallization from cold (−30° F., −35° C.) hexane which gave the product as dark plates. NMR Characterization. $^1$H NMR (C$_6$D$_6$, ppm, approximate coupling constants for the diene protons were determined by simulation): δ3.73 (m, CH(CH$_3$)CHCHCH(CH$_3$), 2H, J$_{HH}$=12 and 10.5 Hz); 2.1 (m, partially overlapped by a C$_5$Me$_4$singlet, CH(CH$_3$)CHCHCH(CH$_3$), 2H); 2.11 (s, C$_5$Me$_{4, 6}$H); 1.89 (d, CH(CH$_3$)CHCHCH(CH$_3$), 6H, J$_{HH}$= 5.4 Hz), 1.24(s, C$_5$Me$_{4, 6}$H); 1.13 (s, $^t$Bu, 9H); 0.73 (s, SiMe$_2$, 6H). The spectrum is illustrated in FIG. 3. The Δd as determined by X-ray crystallography is −0.11 Å, verifying that the compound is a π-complex.

EXAMPLE 19

Synthesis of (C$_5$Me$_4$SiMe$_2$NPh)Ti(s-trans-$\eta^4$-trans-1,3-pentadiene)

In an inert atmosphere glove box, 250 mg (0.64 mmol) of (C$_5$Me$_4$SiMe$_2$NPh)TiCl$_2$ and 1.3 mL (13 mmol) of technical grade 1,3-pentadiene was dissolved in 30 mL of hexanes. 0.51 mL of 2.5M n-BuLi (1.3 mmol) was added to the yellow solution which turned dark immediately. After stirring at room temperature for 15 minutes the solution was warmed to about 60° C. for 45 minutes. A gray precipitate was visible. The mixture was filtered through Celite™. The solvent was removed from the filtrate under reduced pressure. The solid residue was redissolved in hexanes and heated to reflux for 2.5 hours. The hexanes were removed under reduced pressure to give a solid residue. The residue was dissolved in a minimum quantity of hexanes and the resulting solution was placed in the freezer (−25° C.). A dark mass of crystals formed from which the solution was decanted. The crystals were redissolved in a minimum of hexanes and placed in the freezer. Purple crystals formed and were separated from the solution by decanting. After drying under reduced pressure, 60 mg (16 percent yield) of purple crystals were isolated. The product was identified by proton NMR spectroscopy to be a 60/40 mixture of isomers (either the s-trans/s-cis isomers or prone/supine s-cis isomers) of (phenylamido)(tetramethyl-$\eta^5$-cyclopentadienyl)dimethylsilanetitanium ($\eta^4$-1,3-pentadiene).

EXAMPLE 20

Synthesis of (C$_5$Me$_4$SiMe$_2$N(C$_6$H$_5$)Ti($\eta^4$-1,4-trans, trans-diphenyl-1,3-butadiene)

In an inert atmosphere glove box, 100 mg (0.258 mmol) of (C$_5$Me$_4$SiMe$_2$NPh)TiCl$_2$ and 53.1 mg (0.258 mmol) of 1,4-trans, trans-diphenyl- 1,3-butadiene was dissolved in 30 mL of hexanes. To this solution was added 0.21 mL of 2.5M (0.52 mmol) n-butyllithium. The solution turned dark immediately. After stirring at room temperature for 15 minutes, the solution was heated to reflux for 45 minutes. The mixture was filtered through Celite™ filter aid to give a dark blue filtrate. Volatiles were removed under reduced pressure to give a dark solid residue. Proton NMR analysis showed the material to be a 45/55 mixture of isomers (either the s-trans/s-cis isomers or prone/supine s-cis isomers) of (phenylamido)(tetramethyl-$\eta^5$-cyclopentadienyl)dimethylsilanetitanium ($\eta^4$-1,4-trans, trans-diphenyl-1,3-butadiene), with approximately 40 mole percent free diene.

EXAMPLE 21

Synthesis of [(N-t-Butyl-amino)(dimethyl)(tetrahydro-fluorenyl) silane]Titanium ($\eta^4$-1,4-trans, trans-diphenyl-1,3-butadiene)

In the drybox in a 100 mL flask 1.0 g (2.4 mmol) of (C$_{13}$H$_{12}$SiMe$_2$N$^t$Bu)TiCl$_2$ was stirred with 0.495 g (2.4 mmol) of trans, trans- 1,4-diphenyl- 1,3-butadiene in about 50 mL of hexane. Then 1.94 mL (4.8 mmol) of 2.48M n-BuLi was added by syringe to the stirring solution which was refluxed for 1½ hours. The solution was filtered over a fine frit and the residue was washed with hexane. The hexane was then removed from the filtrate by vacuum distillation leaving a dark green solid. After trituration with hexane the solid was dried under vacuum to yield 1.12 g (84.8 percent) of (C$_{13}$H$_{12}$SiMe$_2$N$^t$Bu)Ti($\eta^4$-1,4-trans, trans-diphenyl-1,3-butadiene) which was identified by its $^1$H NMR spectrum.

EXAMPLE 22

Synthesis of [(N-t-butyl-amino)(dimethyl)(1,3-dimethyl-4,5,6,7-tetrahydroindenyl)silane] titanium ($\eta^4$-1,4-trans, trans-diphenyl-1,3-butadiene)

Step 1: Preparation of 4,5,6,7-tetrahydro-1-methyl-indan-3-one

Cyclohexene (27.3 g, 0.33 mol), crotonic acid (28.7 g, 0.33 mol) and polyphosphoric acid (300 mL) were mechanically stirred under a nitrogen atmosphere at 60° C. for 30 minutes. The slurry was poured into water and the aqueous solution extracted with diethyl ether. The diethyl ether extract was washed successively with a 10 percent NaHCO$_3$ solution and a saturated NaCl solution. The organic extract was dried over anhydrous MgSO$_4$. The solution was filtered and the solvent removed under reduced pressure. The crude product was purified via vacuum distillation (bp 87°–92° C. at 5 mm) to give 32.6 g (66 percent) of purified material.

Step 2: Preparation of 7,9dimethylbicyclo-[4.3.0]-nona-1(6),7-diene

Methyl lithium (96 mL, 1.5M, 0.144 mol) was added dropwise to a solution of 4,5,6,7-tetrahydro-1-methyl-indan-3-one (17.7 g, 0.118 mol) in 50 mL of diethyl ether under an argon atmosphere whereupon the reaction mixture was refluxed for 18 hours. The mixture was hydrolyzed, and extracted with diethyl ether. The ether extracts were dried over anhydrous $MgSO_4$ and filtered. To the ether solution 0.5 mL of 6M HCl was added and the solution was stirred for one hour. After this time period the ether solution was washed with water, dried over anhydrous $MgSO_4$, filtered, and concentrated. Distillation at reduced pressure afforded 8.0 g (45 percent) of product.

Step 3: Preparation of lithium 1,3-dimethyl-4,5,6,7-tetrahydroindenide 7,9 dimethylbicyclo-[4.3.0]-nona-1(6),7-diene (5.0 g, 33.5 mmol) was added to 100 mL of pentane. To this solution nBuLi (2.7M, 13 mL) was added dropwise, and the mixture was stirred for 12 hours. The resulting white precipitate was collected via filtration, washed with pentane and dried under reduced pressure to give 5.02 g (97 percent) of product.

Step 4: Preparation of (N-t-butylamino)(dimethyl)(1,3-dimethyl-4,5,6,7-tetrahydroindenyl)silane In an argon atmosphere drybox 0.77 g of $ClSiMe_2NHCMe_3$ (4.67 mmol) was added to 50 mL of THF. To this solution 0.75 g (4.67 mmol) of lithium 1,3-dimethyl-4,5,6,7-tetrahydroindenide was added. The solution was then brought to reflux for about 3 hours and then cooled to room temperature. Chromatographic analysis showed the reaction to be complete. The solvent was then removed under reduced pressure. The residue was extracted with pentane, filtered, and the solvent again removed under reduced pressure to give 1.21 g of product (94 percent yield).

Step 5: Preparation of (N-t-butylamino)(dimethyl)(1,3-dimethyl-4,5,6,7-tetrahydroindenyl)silane $(MgCl)_2 \cdot Et_2O$ In the drybox under argon atmosphere 1.44 g (5.2 mmol) of (N-t-butylamino)(dimethyl)( 1,3-dimethyl-4,5,6,7-tetrahydroindenyl)silane was stirred in 45 mL toluene. To this solution 4.6 mL (10.3 mmol) of isopropyl magnesium chloride (2.24M in ether) was added, stirred, and refluxed for about 2½ hours. The toluene was then stripped off under vacuum while hot, and the remaining gray solid was washed with hexane. The solid was filtered out and washed with excess hexane leaving a light gray powder on the frit, The product weighed 1.94 g (80 percent yield). Molecular weight as determined by titration was 465 g/mol.

Step 6: Preparation of [(N-t-butylamino)(dimethyl)(1,3-dimethyl-4,5,6,7-tetrahydroindenyl)silane]titanium dichloride In the drybox in an argon atmosphere 2.36 g (6.36 mmol) of $TiCl_3(THF)_3$ was dissolved in 100 mL of THF. To this solution 1.84 g (6.36 mmol) of (N-t-butylamino)(dimethyl)(1,3-dimethyl-4,5,6,7-tetrahydroindenyl)silane(MgCl)$_2 \cdot Et_2O$ was added as a solid while stirring. After continued stirring for 15 minutes 0.88 g of $PbCl_2$ (3.18 mmol) was added and stirring continued for 30 minutes. THF was then removed under reduced pressure. The residue was extracted with hexane and filtered to remove the residual magnesium salts. The hexane was then stripped off leaving the product as a brown/orange solid weighing 0.96 g, 38 percent yield. The product was identified by its $^1H$ NMR spectrum.

Step 7: Preparation of [(N-t-butylamino)(dimethyl)(1,3-dimethyl-4,5,6,7-tetrahydroindenyl)silane] titanium ($\eta^4$-1, 4-trans, trans-diphenyl-1,3-butadiene)

In the drybox in an argon atmosphere 0.01 g of lithium metal (1.6 mmol) and 0.11 g of trans,trans-1,4-diphenyl-1, 3-butadiene (0.5 mmol) were stirred together in 30 mL of diethyl ether for about 25 minutes. After this time 0.20 g (0.5 mmol) of $(C_{11}H_{14}SiMe_2N^tBu)TiCl_2$ was added and stirred about 45 minutes producing a dark red/brown solution. The ether was removed under vacuum and the product was extracted with hexane. The solids were filtered and hexane was stripped off leaving a dark red/purple compound. The product weighed 0.033 g, 11 percent yield. The identity of the product was determined by its $^1H$ NMR spectrum.

EXAMPLE 23

Synthesis of $(C_5Me_4SiMe_2N^tBu)Zr(\eta^4$-1,4-trans, trans-diphenyl-1,3-butadiene)

In an inert atmosphere glove box 0.100 g of $(C_5Me_4SiMe_2N^tBu)ZrCl_2$ (0.0243 mmol) was dissolved into 30 mL of diethyl ether followed by addition of 0.050 g of trans, trans-1,4-diphenyl-1,3-butadiene (0.243 mmol) and 0.0051 g of Li metal (0.729 mmol). 5 to 10 mL of additional $Et_2O$ was used to aid in the transfer of each of the latter reagents. After 30 minutes the color of the reaction was a reddish orange color. After this time the solvent was removed under reduced pressure and the product extracted with hexane until the filtrate was colorless. The combined filtrate was taken to dryness under reduced pressure, giving the product as a reddish orange solid. The product was characterized by its $^1H$ NMR spectrum as a 60/40 mixture of isomers (either the s-trans/s-cis isomers or prone/supine s-cis isomers).

General Polymerization Conditions Using Complexes from Examples 16–19 and 21–23, Runs A–O A two-liter Parr reactor was charged with 740 g of Isopar™ E mixed alkanes solvent and 118 g of 1-octene comonomer. Hydrogen was added as a molecular weight control agent by differential pressure expansion from an about 75 mL addition tank at 25 psi (170 kPa). The reactor was heated to the polymerization temperature of 140° C. and saturated with ethylene at 500 psig (3.45 MPa). 2.0 µmol each of catalyst and cocatalyst (0.005M solutions in toluene) were premixed in the drybox for the time periods indicated. After the desired premix time, the solution was transferred to a catalyst addition tank and injected into the reactor. The polymerization conditions were maintained for 15 minutes with ethylene on demand. The resulting solution was removed from the reactor, and a hindered phenol antioxidant (Irganox™ 1010) was added. Polymers were recovered by removing solvent in a vacuum oven set at 120° C. for about 20 hours. Results are contained in Table II.

TABLE II

| run | Complex | Co-catalyst | mix time (h) | yield (g) | efficiency Kg/g |
|---|---|---|---|---|---|
| A | ex. 16[1] | TPFB | | 50.1 | 523 |
| B | " | TPFB | 2 | 45.5 | 474 |
| C | ex. 17[2] | TPFB[8] | | 116.2 | 1213 |
| D | ex. 18[3] | TPFB | | 131.0 | 1367 |
| E | ex. 19[4] | TPFB | | 5.3 | 55 |
| F | ex. 21[5] | ATPFB[9] | 0.25 | 42.1 | 439 |
| G | " | ATPFB | 1 | 58.4 | 610 |
| H | " | ATPFB | 19 | 56.0 | 585 |
| I | " | TPFB | | 4.5 | 47 |
| J | " | TPFB | 0.5 | 31.3 | 327 |
| K | " | TPFB | 2 | 44.6 | 466 |
| L | ex. 22[6] | ATPFB | 2.5 | 23.1 | 241 |
| M | " | ATPFB | 5 | 97.1 | 1014 |
| N | " | TPFB | 0.5 | 3.3 | 34 |
| O | ex. 23[7] | TPFB | | 7.1 | 16 |

[1]$(C_5Me_4SiMe_2N^tBu)Ti(\eta^4$-3-methyl-1,3-pentadiene)

TABLE II-continued

| run | Complex | Co-catalyst | mix time (h) | yield (g) | efficiency Kg/g |
|-----|---------|-------------|--------------|-----------|-----------------|

[2] $(C_5Me_4SiMe_2N^tBu)Ti(\eta^4$-1,3-pentadiene)
[3] $(C_5Me_4SiMe_2N^tBu)Ti(\eta^4$-2,4-hexadiene)
[4] $(C_5Me_4SiMe_2NPh)Ti(\eta^4$-1,3-pentadiene)
[5] $(C_{13}H_{12}SiMe_2N^tBu)Ti(\eta^4$-1,4-trans,trans-diphenyl-1,3-butadiene)
[6] $(C_{11}H_{14}SiMe_2N^tBu)Ti(\eta^4$-1,4-trans,trans-diphenyl-1,3-butadiene)
[7] $(C_5Me_4SiMe_2NtBu)Zr(\eta^4$-1,4-trans,trans-diphenyl-1,3-butadiene) 5 μmol used
[8] trispentafluorophenylborane, $B(C_6F_5)_3$?
[9] anilinium tetrakispentafluorophenylborate, $[NHMe_2Ph][B(C_6F_5)_4]$

EXAMPLE 24

Preparation of
$[(Me_4C_5)SiMe_2N^tBu]Ti[\eta^4$-1-(4-$^tBu$-$C_6H_4$)-4-phenyl-trans, trans-1,3-butadiene]

Diene Preparation

This material was prepared by a modification of the general method described by Ballistreri et. al., *J. Chem. Soc., Perkin Trans.* 2, 1982, 273.

A) 4-$^tBuC_6H_4CH_2PPh_3Br$

To 500 mL of xylenes in a 2 liter 3-necked round bottomed flask was added 25 g of 4-$^tBuC_6H_4CH_2Br$ (Aldrich and 38 g triphenylphosphine ($PPh_3$) (Aldrich). The mixture was heated to reflux overnight then cooled to room temperature and filtered. The solid collected on the filter was washed with xylene and dried under reduced pressure overnight.

B) 1-(4-tert-butylphenyl)-4-phenyl-trans, trans-1,3-butadiene

A nitrogen-purged 2 liter 3-necked round bottomed flask was charged with 500 mL of anhydrous ethanol. Lithium wire (0.8 g) was added and allowed to dissolve with stirring. To this solution was added 53.8 g of 4-$^tBuC_6H_4CH_2PPh_3Br$ followed by 15.3 g of trans-cinnamaldehyde (Aldrich). The mixture was stirred at room temperature overnight. The next day, 300 mL of water was added and the mixture stirred for 30 minutes. The mixture was then filtered, resulting in the collection of off-white crystals on the filter. These crystals were washed with a 60/40 ethanol/water mixture then dried in a vacuum oven overnight. 1-(4-$^tBu$-$C_6H_4$)-4-phenyl-trans, trans-1,3-butadiene was identified by its mass spectrum, m/z=262.1 for the parent ion.

Complex Preparation

In the drybox, 0.25 g of 1-(4-$^tBuC_6H_4$)-4-phenyl-trans, trans-1,3-butadiene and 0.37 g of $[(Me_4C_5)SiMe_2N^tBu]TiCl_2$ were dissolved/suspended in 30 mL of anhydrous hexane. To this was added 1.01 mL of $^nBuLi$ (about 1.89M in hexane by titration (Aldrich Chemical Co.). The color immediately darkened. The mixture was heated to a gentle reflux with stirring. After one hour, the mixture was filtered through a medium porosity fritted funnel using Celite™ brand filter aid. The hexane was evaporated under reduced pressure to leave a deep purple slightly sticky solid. The $^1H$ NMR spectrum of this material confirmed its identity as the desired compound, containing some unreacted 1-(4-$^tBuC_6H_4$)-4-phenyl-trans, trans-1,3-butadiene. $^1H$ NMR characterization for $[(Me_4C_5)SiMe_2N^tBu]Ti[\eta^4$-1-($^tBuC_6H_4$)-4-phenyl- 1,3-butadiene] ($C_6D_6$): 7.4–7.2 ppm (m, $C_6\underline{H}_5$ and $^tBuC_6\underline{H}_4$); 7.0–6.8 ppm (m, $C_6\underline{H}_5$ and $^tBuC_6\underline{H}_4$); 4.65, 4.05 ppm (multiplets, $^tBuC_6H_4\underline{CHCHCHC}$H$Ph$); 1.67, 1.63, 1.27, 1.25 ppm (s, $C_6\underline{Me}_4$); 1.38 ppm (s, N$^t\underline{Bu}$); 1.29 ppm (s, $^t\underline{Bu}C_6H_4$); 0.61 ppm (s, $SiMe_2$, 6H).

EXAMPLE 25

Ethylene/styrene copolymerization using
(tert-butylamido)(tetramethyl-$\eta$
5-cyclopentadienyl)-dimethylsilanetitanium
(s-trans-$\eta^4$-1,4-trans, trans-diphenyl-1,3-butadiene)

A 2 L stirred reactor was charged with 361 g of Isopar™ E and 458 g of styrene comonomer. Hydrogen was added by differential pressure expansion from a 75 mL addition tank initially at 2070 kPa to 1393 kPa. The reactor was heated to 80° C. and saturated with ethylene at 1380 kPa. The catalyst was prepared in a dry box by adding 3.5 μmol of tris(pentafluorophenyl)borane (700 μL of a 0.0050M solution in toluene) to 3.5 μmol of (tert-butylamido)(tetramethyl-$\eta^5$-cyclopentadienyl)dimethylsilanetitanium ($\eta^4$-1,4-trans, trans-diphenyl-1,3-butadiene)in toluene. This mixture was then transferred to a catalyst addition tank and injected into the is reactor. The polymerization was allowed to proceed with ethylene on demand. After 10 minutes an additional 3.5 μmol of catalyst solution was injected into the reactor. After a total of 20 minutes the polymer solution was removed from the reactor and quenched with isopropyl alcohol. Irganox™ 1010 was added to the polymer solution. The polymer solution was devolatilized in a vacuum oven at 120° C. for about 20 hours. 58 g of polymer having a melt index, $I_2$, of 0.4 and styrene content of 37 percent was recovered.

EXAMPLE 26

Ethylene/1-octene Copolymerization Using
(tert-butylamido)(tetramethyl-$\eta$
5-cyclopentadienyl)-dimethylsilanetitanium
($\eta^4$-1,3-pentadiene)

A 1 gallon (3.8 L) stirred reactor was charged with 2 L of Isopar™ E and 175 mL of 1-octene. 100 Δpsig (690 kPa) of hydrogen was added by differential pressure expansion from a 30 mL addition tank. The reactor was heated to 140° C. and saturated with ethylene to 450 psig (3.10 MPa). The catalyst mixture was prepared in a drybox by syringing together 1 mL of 0.0050M $[(Me_4C_5)SiMe_2N^tBu]Ti(\eta^4$-1,3-pentadiene) solution (in Isopar™ E), 1.5 mL of a 0.01M $(C_6F_5)_3B$ solution (in Isopar™ E), and 1 mL of a 0.05M modified methylalumoxane solution (in heptane). This solution was then transferred by syringe to a catalyst addition tank and injected into the reactor. The polymerization was allowed to proceed for 10 minutes and the polymer solution was drained from the reactor. Irganox ™ 1010 anti-oxidant was added and the polymer was air-dried followed by drying in a reduced pressure oven. Yield: 146 g of ethylene consumed. Efficiency was 610,000 g ethylene consumed/g Ti.

EXAMPLE 27

Ethylene/propylene Copolymerization Using
(tert-butylamido)(tetramethyl-$\eta$
5-cyclopentadienyl)dimethylsilanetitanium
(s-trans-$\eta^4$-1,4-trans, trans-diphenyl- 1,3-butadiene)

A 1 gallon (3.8 L) stirred reactor was charged with 2 L of Isopar™ E and 40 g of propylene. 50 Δpsig (345 kPa) of hydrogen was added by differential pressure expansion from a 30 mL addition tank. The reactor was heated to 140° C. and saturated with ethylene to 450 psig (3.10 MPa). The catalyst mixture was prepared in a drybox by syringing together 1 mL of 0.0050M $[(Me_4C_5)SiMe_2N^tBu]$-Ti(s-trans-$\eta^4$-1,4-trans, trans-diphenyl-1,3-butadiene) solution (in Isopar™

E), 1.5 mL of a 0.01M $(C_6F_5)_3B$ solution (in Isopar™ E), and 1 mL of a0.05M MMAO solution (in heptane). This solution was then transferred by syringe to a catalyst addition tank and injected into the reactor. The polymerization was allowed to proceed for 10 minutes and the polymer solution was drained from the reactor. A hindered phenol anti-oxidant was added and the polymer was air-dried followed by drying in a reduced pressure oven. Yield: 169 g of polymer having a density of 0.916 g/mL; melt index $(I_2)$: 0.5; $I_{10}/I_2$: 8.0. Efficiency was 706,000 g polymer/g Ti.

EXAMPLE 28

Ethylene/propylene Copolymerization Using (tert-butylamido)(tetramethyl-η
s-cyclopentadienyl)dimethylsilanetitanium
(s-trans-$\eta^4$-1,4-trans, trans-diphenyl- 1,3-butadiene)

A 1 gallon (3.8 L) stirred reactor was charged with 2 L of Isopar™ E mixed alkanes and 80 g of propylene. 50 Δpsig (345 kPa) of hydrogen was added by differential pressure expansion from a 30 mL addition tank. The reactor was heated to 110° C. and saturated with ethylene to 450 psig (3.1 MPa). The catalyst mixture was prepared in a drybox by syringing together 1 mL of 0.0050M [(Me$_4$C$_5$)SiMe$_2$N$^t$Bu]Ti(s-trans-$\eta^4$-1,4-trans, trans-diphenyl-1,3-butadiene) solution (in Isopar™ E), 1.5 mL of a 0.01M $(C_6F_5)_3B$ solution (in Isopar™ E), and 1 mL of a 0.05M MMAO solution (in heptane). This solution was then transferred by syringe to a catalyst addition tank and injected into the reactor. The polymerization was allowed to proceed for 10 minutes and the polymer solution was drained from the reactor. A hindered phenol anti-oxidant was added and the polymer was air-dried followed by drying in a reduced pressure oven. Yield: 272 g of polymer; efficiency: 1,140,000 g polymer/g Ti; density: 0.900 g/mL; melt index $(I_2)$: 1.0; $I_{10}/I_2$: 7.1.

EXAMPLE 29

Ethylene/1-Octadecene Copolymerization Using (tert-butylamido)(tetramethyl-η
s-cyclopentadienyl)dimethylsilanetitanium
(s-trans-$\eta^4$-1,4-trans, trans-diphenyl- 1,3-butadiene)

A 1 gallon (3.8 L) stirred reactor was charged with 2 L of Isopar™ E and 600 mL of 1-octadecene. 50 Δpsig (345 kPa) of hydrogen was added by differential pressure expansion from a 30 mL addition tank. The reactor was heated to 120° C. and saturated with ethylene to 450 psig (3.1 MPa). The catalyst mixture was prepared in a drybox by syringing together 2 mL of 0.0050M [(Me$_4$C$_5$)SiMe$_2$N$^t$Bu]Ti(s-trans-$\eta^4$-1,4-trans, trans-diphenyl-1,3-butadiene) solution (in Isopar™ E), 3 mL of a 0.01M $(C_6F_5)_3B$ solution (in Isopar™ E), and 2 mL of a 0.05M modified MAO solution (in heptane). This solution was then transferred by syringe to a catalyst addition tank and injected into the reactor. The polymerization was allowed to proceed for 10 minutes and the polymer solution was drained from the reactor. A hindered phenol anti-oxidant was added and the polymer was air-dried followed by drying in a reduced pressure oven. Yield: 134 g of ethylene consumed; efficiency: 280,000 g ethylene consumed/g Ti; density: 0.903 g/mL; melt index $(I_2)$: 0.7; $I_{10}/I_2$: 7.5.

EXAMPLE 30

Ethylene/Octene/Ethylidene Norbornene Copolymerization Using (tert-butylamido)(tetramethyl-η
s-cyclopentadienyl)dimethylsilanetitanium (s-trans-η
4-1,4-trans, trans-diphenyl-1,3-butadiene)

A 1 gallon (3.8 L) stirred reactor was charged with 1132 g of Isopar™ E, 498 g of 1-octene, and 100 mL of ethylidene norbornene. The reactor was heated to 120° C. and saturated with ethylene to 430 psig (3.0 MPa). The catalyst mixture was prepared in a drybox by syringing together 2 mL of 0.0050M [(Me$_4$C$_5$)SiMe$_2$N$^t$Bu]Ti(s-trans-$\eta^4$-1,4-trans, trans-diphenyl-1,3-butadiene) solution (in Isopar™ E), 2 mL of a 0.015M $(C_6F_5)_3B$ solution (in Isopar™ E), and 2 mL of a 0.05M MMAO solution (in heptane). This solution was then transferred by syringe to a catalyst addition tank and injected into the reactor. The polymerization was allowed to proceed for 25 minutes and the polymer solution was drained from the reactor. A hindered phenol anti-oxidant was added and the polymer was air-dried followed by drying in a reduced pressure oven. Yield: 85.8 g of ethylene consumed; efficiency: 179,000 g ethylene consumed/g Ti; density: 0.874 g/mL; melt index $(I_2)$: 1.4; $I_{10}/I_2$: 6.7.

EXAMPLE 31

Dual Catalyst Polymerization

A) Heterogeneous Catalyst Preparation

A heterogeneous Ziegler-type catalyst was prepared substantially according to U.S. Pat. No. 4,612,300, Ex. P., by sequentially adding to a volume of Isopar™ E, a slurry of anhydrous magnesium chloride in Isopar™ E, a solution of $C_2H_5AlCl_2$ in hexane, and a solution of titanium tetraisopropoxide (Ti(O$^i$Pr)$_4$) in Isopar™ E, to yield a composition containing a magnesium concentration of 0.17M and a ratio of Mg/Al/Ti of 40/12/3. An aliquot of this composition containing 0.045 mMol of Ti was treated with a dilute solution of Et$_3$Al to give an active catalyst with a final Al/Ti ratio of 12/1.

B) Polymerization

A stirred, one-gallon (3.81) autoclave reactor was charged with 2.1 L of Isopar™ E and 300 mL of 1-octene and the contents were heated to 120° C. The reactor was next charged with ethylene sufficient to bring the total pressure to 450 psig (3.1 MPa). The catalyst mixture was prepared in a drybox by syringing together 2 mL of 0.0050M [(Me$^4$C$_5$)SiMe$_2$N$^t$Bu]Ti(s-trans-η $^4$-1,4trans, trans diphenyl-1,3-butadiene) solution (in Isopar™ E), 2 mL of a 0.015M $(C_6F_5)_3B$ solution (in Isopar™ E), and 2 mL of a 0.05M MMAO solution (in heptane). This solution was then transferred by syringe to a catalyst addition tank and injected into the reactor. The reactor temperature and pressure were maintained at 450 psig (3.1 MPa) and 120° C. by continually feeding ethylene during the polymerization run and cooling the reactor as necessary. After a 10 minute reaction time, the ethylene was shut off and the reactor was depressurized to 100 psig (690 kPa). 250 Δpsig (1.7 MPa) of hydrogen was added by differential pressure expansion from a 30 mL addition tank. An aliquot of the heterogeneous catalyst containing 0.009 mmol Ti prepared as described in the catalyst preparation section was injected into the reactor. The reactor was then continually fed ethylene at 450 psig (3.10 MPa) and the reaction temperature quickly rose to 190° C. where the polymerization was sustained for an additional 10 minutes. The polymer solution was drained from the reactor, and a hindered phenol anti-oxidant was added and the polymer was air-dried followed by drying in a reduced pressure oven. Yield: 271 g of polymer; efficiency: 404,000 g polymer/g Ti.

EXAMPLE 32

Slurry Polymerization

A) Support Preparation

A sample of spherical agglomerated silica gel (Grace Davison SMR 390-2144-Item B, median particle size=10 μm) was dehydroxylated at 750° C. under nitrogen for 12 h in a fluidized bed. To 20 g of the silica was added 50.6 mL of a toluene solution of methylaluminoxane (Akzo, 6.7 wt percent Al) followed by 150 mL of hexane. The resulting slurry was stirred under nitrogen for 24 h, the solid was allowed to settle and the supernatant was decanted. The solid was then washed with 3×150 mL portions of hexane followed by drying under vacuum at 100° C. for 24 h. The resulting solid was analyzed for aluminum and found to contain 7.48 percent.

B) Catalyst Preparation

1): To 1 g of the above support was added 11.4 mL of a solution of $[(Me_4C_5)SiMe_2N^tBu]Ti(s-trans-\eta^4-1,4-trans, trans-diphenyl-1,3-butadiene)$ (3.73 mM in hexane) and the slurry was stirred for 2 hr prior to the addition of 1.95 mL of $(C_6F_5)_3B$ (0.041M in Isopar™ E). The slurry was then stirred for a further 12 hr prior to drying at room temperature under vacuum. The catalyst had a Ti concentration of 42.5 μmol/g support and a Boron:Ti molar ratio of 1.9:1.

2): To 1 g of the above support was added 22.8 mL of a solution of $[(Me_4C_5)SiMe_2N^tBu]Ti(s-trans-\eta^4-1,4-trans, trans-diphenyl-1,3-butadiene)$ (3.73 mM in hexane) and the slurry was stirred for 2 h prior to the addition of 3.89 mL of $(C_6F_5)_3B$ (0.041M in Isopar™ E). The slurry was then stirred for a further 12 h prior to drying at room temperature under vacuum. The catalyst had a Ti concentration of 85 μmol/g support and a Boron:Ti molar ratio of 1.9:1.

C) Polymerization

A stirred 5 L autoclave reactor was charged with 1850 g of anhydrous hexane and optionally butene (as identified in Table III) through a mass-flow meter. A solution containing 100 μmoles of modified methylaluminoxane (MMAO, Akzo) in 10 mL of hexane was then added to the reactor via a pressurized stainless steel cylinder prior to heating to 80° C. At this point the reactor pressure was increased 10 psig (70 kPa) by the addition of hydrogen followed by ethylene sufficient to bring the total pressure to 175 psig (1.21 MPa). The ethylene was supplied continuously to the reactor by a demand feed regulator on the line. The required weight of the catalyst was slurried in hexane and was then added to the reactor to initiate the polymerization. After 30 minutes the ethylene flow was stopped and the reactor was vented and cooled. The polymer was filtered and dried at 80° C. overnight in a vacuum oven. After drying and weighing to obtain the catalyst efficiency the samples were stabilized and melt flow measurements obtained using standard ASTM methods. Results are reported in Table III.

TABLE III

| run | Catalyst[1] | butene (g) | yield (g) | efficiency Kg/g Ti | melt index I2 dg/min | melt ratio I10/I2 |
|---|---|---|---|---|---|---|
| P | 32B) 1 | 0 | 99 | 260 | 5.99 | 6.14 |

TABLE III-continued

| run | Catalyst[1] | butene (g) | yield (g) | efficiency Kg/g Ti | melt index I2 dg/min | melt ratio I10/I2 |
|---|---|---|---|---|---|---|
| Q | 32B) 2 | 0 | 160 | 418 | | |
| R | " | 10 | 195 | 509 | 1 | |

[1]$(C_5Me_4SiMe_2NtBu)Ti(\eta^4$-1,4-trans,trans-diphenyl-1,3-butadiene)

GAS PHASE POLYMERIZATION EXAMPLES 33–39

All gas phase polymerizations, unless otherwise noted, were carried out under nitrogen pressures of 15–80psi (100–550 kPa)in a 5 L fluidized bed laboratory reactor. The pressures of ethylene and hydrogen reported refer to partial pressures. The support was powdered, high density ethylene homopolymer or silica treated with aluminum trialkyl. The latter support is prepared according to the technique disclosed in WO-94/03506, which is equivalent to U.S. Ser. No. 07/926,006, pending, the teachings of which are incorporated herein by reference. The metal complex and activating cocatalyst are, respectively, $(C_5Me_4SiMe_2N^tBu)Ti(s-trans-\eta^4$-1,4-trans, trans-diphenyl- 1,3-butadiene) and $B(C_6F_5)_3$.

EXAMPLE 33

Catalyst/support Preparation 2 mL of a 0.005M solution (10 μmol) of $(C^5Me_4SiMe_2N^tBu)Ti(s-trans-\eta^4$-1,4-trans, trans-diphenyl-1,3-butadiene) in toluene and 2.4 mL of a 0.005M solution (12 μmol) of $B(C_6F_5)_3$ in toluene were combined with 0.600 g of 0.33 melt index high density polyethylene powder which previously had been sieved to remove any particles larger than 25 mesh, (0.7 mm). The solvent was removed to give a pale purple free-flowing heterogeneous, catalyst composition.

Polymerization 0.24 g (4 μmol Ti, 4.8 μmol borane) of the catalyst composition was introduced into a fluidized bed reactor containing 260 psi (1.79 MPa) ethylene and 0.65 psi hydrogen (4.5 kPa, 0.25 mol percent based on ethylene) at a temperature of 48° C. There was a reaction exotherm of 1° C. After a run time of 3 hours, 17 g of polyethylene having a melt index of 0.12 was recovered. The productivity was 89,000 g polymer/g Ti.

EXAMPLE 34

Catalyst/support Preparation

A slurry of 5 g non-dehydrated Davison 952 silica in toluene was treated with 1.25 mL of neat triethylaluminum (TEA) resulting in vigorous effervescence. After stirring for 15 minutes the TEA-treated silica was filtered, washed with toluene, then dried under vacuum. To 0.500 g of this silica were added 10 μmol of $(C_5Me_4SiMe_2N^tBu)Ti(s-trans-\eta^4$-1, 4-trans, trans-diphenyl-1,3-butadiene) as a 0.005M toluene solution and 12 μmol of $B(C_6F_5)_3$ as a 0.005M toluene solution. The solvent was removed from the resulting purple slurry to give the catalyst composition as a light purple, free-flowing powder. 0.30 g of the resulting supported catalyst (5 μmol titanium complex, 6 μmol borane complex) was used in the following polymerization.

Polymerization 0.25 g (5 μmol titanium complex, 6 μmol borane complex) of the catalyst composition was introduced into a fluidized bed reactor pressurized to 275 psi (1.90 MPa) with 220 psi (1.52 MPa) ethylene, 18 mol percent butene (based on ethylene) and 0.65 psi hydrogen (4.5 kPa, 0.33 mol percent based on ethylene) with nitrogen making up the remainder of the pressure, at a temperature of 46° C. There was a reaction exotherm of 10° C. After a run time of 2 hours, 119 g of polyethylene having a melt index of 0.11, $M_w/M_n$=2.06, density=0.8891 was recovered. The productivity was 496,000 g polymer/g Ti.

EXAMPLE 35

Catalyst/support Preparation

To 0.250 g of silica treated with triethylaluminum as in Example 34 were added 2 μmol of $(C_5Me_4SiMe_2N^tBu)Ti$(s-trans-$\eta^4$-1,4-trans, trans-diphenyl- 1,3-butadiene) as a 0.005M toluene solution and 6 μmol of $B(C_6F_5)_3$ as a 0.005M toluene solution. The solvents were removed from the resulting slurry to give the catalyst composition as a light purple, free-flowing powder.

Polymerization

The above catalyst composition was introduced into a fluidized bed reactor pressurized to 260 psi (1.79 MPa) with 40 percent ethylene, 2.5 percent butene, 0.13 percent hydrogen, with nitrogen making up the remainder of the pressure, at a temperature of 67° C. There was a reaction exotherm of 28° C. After a run time of 60 minutes, 52 g of polyethylene having a melt index of 0.34, $M_w/M_n$=2.24, and a bulk density of 0.36 g/mL was recovered. The productivity was 540,000 g polymer/g Ti.

EXAMPLE 36

Polymerization

The polymerization was carried out analogously to Example 35, except that the butene concentration was 1.25 percent and the initial temperature was 93° C. After a run time of 64 minutes, 29 g of polyethylene having a melt index of 0.62 and a $M_w/M_n$=2.31 was recovered.

EXAMPLE 37

Catalyst/support Preparation

A catalyst composition was prepared as in Example 34, except that 0.25 g of Davison 162 silica (treated with triethylaluminum as in Example 34), 5 μmol of $(C_5Me_4SiMe_2N^tBu)Ti$(s-trans-$\eta^4$-1,4-trans, trans-diphenyl-1,3-butadiene) and 10 μmol of $B(C_6F_5)_3$ were used.

Polymerization

The above catalyst composition was introduced into a fluidized bed reactor pressurized to 260 psi (1.79 MPa) with 82.5 percent ethylene, 2.5 percent butene, 0.21 percent hydrogen, with nitrogen making up the remainder of the pressure, at a temperature of 59° C. After a run time of 15 minutes, 8 g of polyethylene having a melt index of 0.20, and a $M_w/M_n$=2.50 was recovered. The productivity was 100,000 g polymer/g Ti/h.

EXAMPLE 38

Catalyst/support Preparation

To 5 g of Davison 952 silica, which had been dried overnight at 150° C., in 125 mL toluene was added 1.25 mL TEA. After reacting for 15 minutes the mixture was filtered, washed with about 50 mL toluene, then dried under vacuum.

To 0.008 g of the above TEA-treated silica were added 3.00 mL of 0.005M (15 μmol) $B(C_6F_5)_3$ in hexane, then 1.00 mL of 0.005M (5 μmol) $(C_5Me_4SiMe_2N^tBu)Ti$(s-trans-$\eta^4$-1,4-trans, trans-diphenyl-1,3-butadiene) in hexane. After stirring for 10 minutes the solvent was removed under vacuum to give the supported catalyst as a free-flowing powder. Additional TEA-treated silica was mixed in as a diluent to give a final weight of 0.200 g.

Polymerization 0.08 of the above supported catalyst (6 μmol borane/2 μmol Ti/0.003 g silica with 0.077 g silica diluent) was introduced into a fluidized bed reactor pressurized to 260 psi (1.79 MPa) with 80.0 percent ethylene, 2.0 percent butene, 0.27 percent hydrogen, with nitrogen making up the remainder of the pressure, at a temperature of 62° C. After a run time of 68 minutes, 27 g of uniform free-flowing polyethylene powder having a melt index of 0.22 and a bulk density=0.40 was recovered. The productivity was 280,000 g polymer/g Ti and 9000 g polymer/g silica.

EXAMPLE 39

Catalyst/support Preparation

A catalyst composition was prepared analogously to Example 38 except that 0.003 g of the TEA-treated silica, 1.200 mL (6 μmol) of the $B(C_6F_5)_3$ solution, and 0.400 mL (2 μmol) of the $(C_5Me_4SiMe_2N^tBu)Ti$(s-trans-$\eta^4$- 1,4trans, trans-diphenyl-1,3-butadiene) solution were used. No diluent was used.

Polymerization

The polymerization was carried out analogously to Example 38 at a temperature of 64° C. After a run time of 90 minutes, 10 g of uniform free-flowing polyethylene powder was recovered.

EXAMPLES 40–41 AND COMPARATIVE EXAMPLE

Continuous Solution Polymerization

Ethylene/1-octene copolymers were prepared in a stirred reactor adapted for continuous addition of reactants and continuous removal of polymer solution, devolatilization and polymer pelletization. Additives (1250 ppm calcium stearate, 200 ppm IRGANOX™ 1010, and 800 ppm SANDOSTAB™ P-EPQ (Sandoz Chemicals)) were added prior to pelletization. A representative process flow diagram for the polymerization is shown in FIG. 4.

Figure 4:
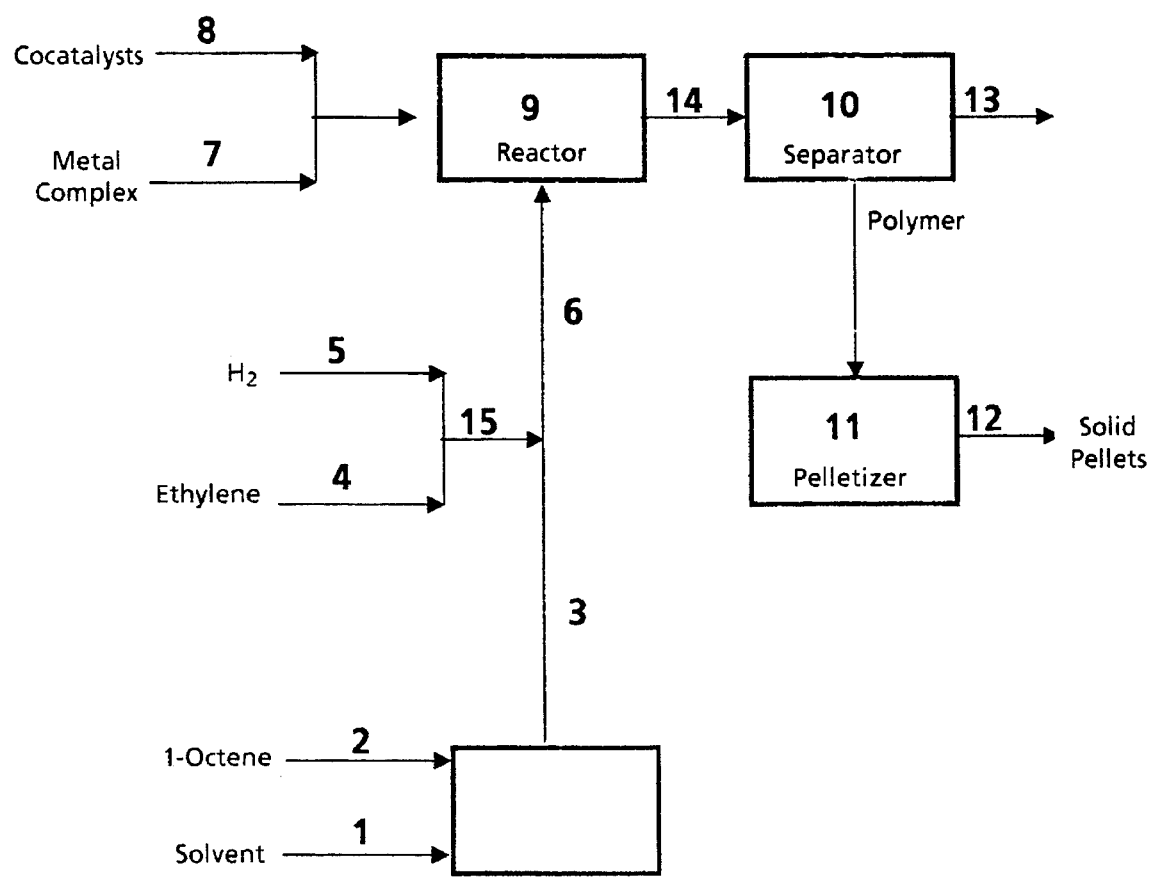
FIG. 4 shows in schematic form the continuous polymerization reactor utilized in Examples 40 and 41 and the comparative example.

In FIG. 4, ethylene (4) and hydrogen (5) are combined into one stream (15) before being introduced into the diluent mixture (3) comprising solvent (Isopar™ E) (1) and 1-octene (2). This combined feed mixture (6) is continuously injected into the reactor (9). The metal complex (7) and cocatalysts (8) are combined into a single stream and also continuously injected into the reactor. The reactor pressure is held constant at about 490 psig (3.38 MPa). Ethylene content of the reactor, after reaching steady state, is maintained below about 8 percent.

The reactor exit stream (14) is continuously introduced into a separator (10), where the molten polymer is separated from the unreacted comonomer(s), unreacted ethylene, unreacted hydrogen, and solvent (13). The molten polymer is subsequently strand chopped or pelletized and, after being cooled in a water bath or pelletizer (11), the solid pellets are collected (12). Additional polymerization conditions and resultant polymer properties are disclosed in Table IV.

TABLE IV

| | Comp. | Ex. 40 | Ex. 41 |
|---|---|---|---|
| Catalyst | TDM[1] | TPB[2] | TPB[2] |
| cocatalyst | TPFB/M[3] | TPFB/M[3] | TPFB/M[3] |
| Ti:B:Al molar ratio | 1:3:6 | 1:4:6 | 1:3:6 |
| Cat. efficiency ($10^6$ kg polymer/kg Ti) | 1.9 | 2.6 | 2.2 |

TABLE IV-continued

|  | Comp. | Ex. 40 | Ex. 41 |
|---|---|---|---|
| $C_2H_4$ conversion per pass (percent) | 86 | 85 | 86 |
| Reactor temperature (°C.) | 130 | 131 | 140 |
| Solvent/$C_2H_4$ feed ratio | 9.0 | 8.4 | 7.8 |
| $C_8H_{16}/C_2H_4 + C_8H_{16}$ feed ratio | 25 | 22 | 23 |
| $H_2$ feed concentration (mol percent) | 0.000 | 0.010 | 0.000 |
| polymer concentration (percent) | 10.0 | 10.3 | 11.2 |
| $C_2H_4$ concentration (percent) | 1.40 | 1.60 | 1.60 |
| $C_2H_4$ feed rate (kg/hr) | 1.2 | 1.2 | 1.2 |
| Melt index ($I_2$) (dg/min) | 0.99 | 1.01 | 1.05 |
| Product $I_{10}/I_2$ | 9.4 | 8.8 | 9.5 |
| Polymer density (g/mL) | 0.9086 | 0.9099 | 0.9107 |

[1] (tert-butylamido)(tetramethyl-η5-cyclopentadienyl)-dimethylsilane-titanium(IV)dimethyl
[2] (tert-butylamido)(tetramethyl(-η5-cyclopentadienyl)-dimethylsilane-titanium(II)(s-trans-η4-1,4-trans,trans-diphenyl-1,3-butadiene)
[3] tris(pentafluorophenyl)borane/MMAO From the results shown in Table IV, it can be seen by comparing Example 40 to the comparative example that at essentially identical reactor temperatures, ethylene conversions, and ethylene concentrations, a higher efficiency was obtained using a complex of the present invention wherein the metal is in the +2 formal oxidation state. Additionally, hydrogen was required in Example 40 to produce polymer of equivalent melt index as that produced in the comparative example. This indicates that the metal complex of the present invention produces higher molecular weight polymers under similar reactor conditions when compared to the use of analogous complexes in the +4 formal oxidation state.

Example 41 demonstrates that polymer of the same melt index as that produced in the comparative example can be produced in the absence of hydrogen by increasing the reaction temperature. Even at the higher reactor temperature of Example 41, the catalyst of the present invention demonstrated a higher catalytic efficiency when compared to the catalyst used in the comparative example.

What is claimed is:

1. A metal complex containing one and only one cyclic delocalized, anionic, π-bonded group, said complex corresponding to the formula:

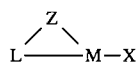

wherein:

M is titanium or zirconium in the +2 formal oxidation state;

L is a group containing a cyclic, delocalized, anionic, π-system through which the group is bound to M, and which group is also bound to Z;

Z is a moiety bound to M via a σ-bond, comprising boron, and the members of Group 14 of the Periodic Table of the Elements, and also comprising an element selected from the groups consisting of an element selected from the groups consisting of nitrogen, phosphorus, sulfur and oxygen, said moiety having up to 60 nonhydrogen atoms; and X is a neutral, conjugated or nonconjugated diene, optionally substituted with one or more groups selected from hydrocarbyl or trimethylsilyl groups, said X having up to 40 carbon atoms and forming a π-complex with M.

2. A complex according to claim 1 corresponding to the formula:

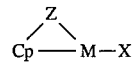

wherein:

Z, M and X are as defined in claim 1, and

Cp is a $C_5H_4$ group bound to Z and bound in an $\eta^5$ bonding mode to M or a substituted $C_5H_4$ group substituted with from one to four substituents independently selected from hydrocarbyl, silyl, germyl, halo, cyano, and combinations thereof, said substituent having up to 20 nonhydrogen atoms, and optionally, two such substituents (except cyano or halo) together cause Cp to have a fused ring structure.

3. A complex according to claim 1 corresponding to the formula:

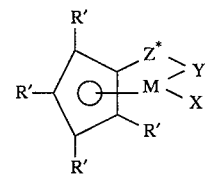

wherein R' each occurrence is independently selected from hydrogen, hydrocarbyl, silyl, germyl, cyano, halo and combinations thereof, said R' having up to 20 non-hydrogen atoms, and optionally two R' groups (when R' is not hydrogen, halo or cyano) together form a divalent derivative thereof connected to adjacent positions of the cyclopentadienyl ring to form a fused ring structure;

X is a neutral $\eta^4$-bonded diene group having up to 30 non-hydrogen atoms, which forms a π-complex with M;

Y is —O—, —S—, —NR*—, —PR*—;

M is titanium or zirconium in the +2 formal oxidation state;

Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$; wherein:

R* each occurrence is independently hydrogen, or a member selected from hydrocarbyl, silyl, halogenated alkyl, halogenated aryl, said R* having up to 10 non-hydrogen atoms, and optionally, two R* groups from Z*, or an R* group from Z* and an R* group from Y (when R* is not hydrogen) form a ring system.

4. A complex according to claim 3 wherein at least one of R' or R* is an electron donating moiety.

5. A complex according to claim 3 wherein Y is a nitrogen or phosphorus containing group corresponding to the formula —N(R")— or —P(R")—, wherein R" is $C_{1-10}$ hydrocarbyl.

6. A metal complex according to claim 5 corresponding to the formula:

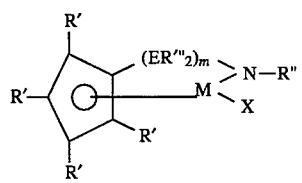

wherein:

M is titanium in the +2 formal oxidation state;

X is s-trans-$\eta^4$-1,4-diphenyl-1,3-butadiene; s-trans-$\eta^4$-3-methyl-1,3-pentadiene; s-trans-$\eta^4$-1,4-dibenzyl-1,3-butadiene; s-trans-$\eta^4$-2,4-hexadiene; s-trans-$\eta^4$- 1,3-pentadiene; s-trans-$\eta^4$-1,4-ditolyl-1,3-butadiene; s-trans-$\eta^4$-1,4-bis(trimethylsilyl)- 1,3-butadiene; s-cis-$\eta^4$-1,4-diphenyl-1,3-butadiene; s-cis-$\eta^4$- 3-methyl-1,3-pentadiene; s-cis-$\eta^4$-1,4-dibenzyl-1,3-butadiene; s-cis-$\eta^4$-2,4-hexadiene; s-cis-$\eta^4$-1,3-pentadiene; s-cis-$\eta^4$-1,4-ditolyl-1,3-butadiene; or s-cis-$\eta^4$-1,4-bis(trimethylsilyl)-1,3-butadiene, said s-cis isomers forming a $\pi$-bound diene complex;

R' each occurrence is independently selected from the group consisting of hydrogen, silyl, hydrocarbyl and combinations thereof said R' having up to 10 carbon or silicon atoms, and optionally two such R' groups (when R' is not hydrogen) together form a divalent derivative thereof connected to adjacent positions of the cyclopentadienyl ring to form a fused ring structure;

R" is $C_{1-10}$ hydrocarbyl;

R''' independently each occurrence is hydrogen or $C_{1-10}$ hydrocarbyl;

E is independently each occurrence silicon or carbon; and m is 1 or 2.

7. A metal complex according to claim 6 wherein R" is methyl, ethyl, propyl, butyl, pentyl, hexyl, norbornyl, benzyl, or phenyl; and the cyclopentadienyl group is cyclopentadienyl, tetramethylcyclopentadienyl, indenyl, tetrahydroindenyl, fluorenyl, tetrahydrofluorenyl or octahydrofluorenyl.

8. A process for preparing a metal complex containing one and only one cyclic delocalized $\pi$-bonded group, said complex corresponding to the formula:

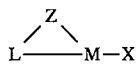

wherein:

M is titanium or zirconium in the +2 formal oxidation state;

L is a group containing a cyclic, delocalized $\pi$-system through which the group is bound to M, and which group is also bound to Z;

Z is a moiety bound to M via a $\sigma$-bond, comprising an element selected from the groups consisting of boron, and the members of Group 14 of the Periodic Table of the Elements, and also comprising an element selected from the group consisting of nitrogen, phosphorus, sulfur and oxygen, said moiety having up to 60 nonhydrogen atoms; and X is a neutral, conjugated or nonconjugated diene, optionally substituted with one or more groups selected from hydrocarbyl or trimethylsilyl groups, said X having up to 40 carbon atoms and forming a $\pi$-complex with M, the steps of the process comprising:
1) a) contacting a conjugated or nonconjugated $C_{4-40}$ diene compound with a metal complex corresponding to the formula:

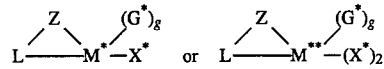

wherein,

M* is titanium or zirconium in the +formal oxidation state;

M** is titanium or zirconium in the +4 formal oxidation state; and

X* is halo;

G* is a neutral Lewis base selected from the group consisting of amines, phosphines and ethers said G having from 3 to 20 nonhydrogen atoms;

Z and L are as previously defined; and g is a number from 0 to 3, in a suitable, noninterfering solvent; and b) contacting the resulting mixture with a reducing agent, or 2) a) contacting a conjugated or nonconjugated $C_{4-40}$ diene compound with a reducing agent in a suitable noninterfering solvent; and b) contacting the resulting mixture with a metal complex corresponding to the formula:

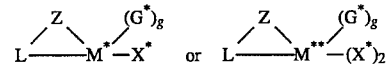

wherein,

M* is titanium or zirconium in the +formal oxidation state;

M** is titanium or zirconium in the +4 formal oxidation state; and

X* is halo;

G* is a neutral Lewis base selected from the group consisting of amines, phosphines and ethers said G having from 3 to 20 nonhydrogen atoms;

Z and L are as previously defined; and g is a number from 0 to 3.

9. A process according to claim 8 wherein the diene compound is selected from the group consisting of 1,4-diphenyl-1,3-butadiene; 3-methyl- 1,3-pentadiene; 1,4-dibenzyl-1,3-butadiene; 2,4-hexadiene; 1,3-pentadiene; 1,4-ditolyl-1,3-butadiene; and 1,4-bis(trimethylsilyl)-1,3-butadiene.

10. A process according to claim 8 wherein the reducing agent is a $C_{1-6}$ lithium alkyl.

11. A process according to claim 8 wherein the reducing agent is lithium.

12. A process according to claim 8 wherein the solvent is a hydrocarbon.

13. A process for preparing a metal complex containing one and only one cyclic, delocalized $\pi$-bonded group, said complex corresponding to the formula:

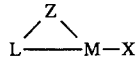

wherein:

M is titanium or zirconium in the +2 formal oxidation state;

L is a group containing a cyclic, delocalized π-system through which the group is bound to M, and which group is also bound to Z;

Z is a moiety bound to M via a σ-bond, comprising an element selected from the groups consisting of boron, and the members of Group 14 of the Periodic Table of the Elements, and also comprising an element selected from the group consisting of nitrogen, phosphorus, sulfur and oxygen, said moiety having up to 60 non-hydrogen atoms; and X is a stable, neutral, conjugated or nonconjugated diene, optionally substituted with one or more groups selected from hydrocarbyl or trimethylsilyl groups, said X having up to 40 carbon atoms and forming a π-complex with M; said process comprising contacting a compound according to the formula $M(X^*)_2$ or a solvated adduct thereof
wherein $X^*$ is halo; and M is as previously defined, with a conjugated or nonconjugated $C_{4-40}$ diene compound corresponding to X and a source of a dianion ligand: $(Z-L)^{-2}$.

14. A process according to claim 13 wherein the compound according to the formula $M(X^*)_2$ is prepared by contacting a compound according to the formula $M^*(X^*)_3$ or $M^{**}(X^*)_4$, or a solvated adduct thereof, in a solvent, with a reducing agent under reducing conditions so as to form the metal complex $MX^*_2$, or a solvated adduct thereof, wherein, $M^*$ is titanium or zirconium in the +formal oxidation state;

$M^{**}$ is titanium or zirconium in the +4 formal oxidation state; and $X^*$ is halo.

* * * * *

UNITED STATES PATENT AND TRADEMARK OFFICE
CERTIFICATE OF CORRECTION

PATENT NO. : 5,470,993
DATED : November 28, 1995
INVENTOR(S) : David D. Devore et al.

It is certified that error appears in the above-indentified patent and that said Letters Patent is hereby corrected as shown below:

Column 39, line 57, following "comprising" insert -- an element selected from the groups consisting of --.

Column 39, line 60, following "from" delete "the groups consisting of an element selected from".

Column 39, line 61, "groups" should correctly read -- group --.

Column 42, line 11 "≠" should correctly read -- +3 --.

Column 42, line 35, "≠" should correctly read -- +3 --.

Column 44, line 11, "≠" should correctly read -- +3 --.

Signed and Sealed this

Eighteenth Day of March, 1997

BRUCE LEHMAN

*Attest:*

*Attesting Officer*   Commissioner of Patents and Trademarks